United States Patent [19]

Grasfield et al.

[11] Patent Number: 6,002,777
[45] Date of Patent: Dec. 14, 1999

[54] ELECTRONIC STETHOSCOPE

[75] Inventors: James A. Grasfield, Sharon; David E. Winston, Winchester; John A. Purbrick, Arlington; Peter R. H. Stark; Daniela Steinhubel, both of Stoneham, all of Mass.

[73] Assignee: StethTech Corporation, Sharon, Mass.

[21] Appl. No.: 09/040,166

[22] Filed: Mar. 17, 1998

Related U.S. Application Data

[60] Division of application No. 08/685,451, Jul. 19, 1996, which is a continuation-in-part of application No. 08/505,601, Jul. 21, 1995, abandoned.

[51] Int. Cl.⁶ ........................................ A61B 7/04
[52] U.S. Cl. .................... 381/67; 181/131; 600/528; D24/134
[58] Field of Search ............... 381/67, 338; 181/131, 181/137; 600/508, 509, 513, 528, 586; D24/134

[56] References Cited

U.S. PATENT DOCUMENTS

| | | | |
|---|---|---|---|
| D. 335,709 | 5/1993 | Choi ........................................ D24/134 |
| D. 389,241 | 1/1998 | Grasfield et al. ....................... D24/134 |
| D. 389,577 | 1/1998 | Grasfield et al. ....................... D24/134 |
| 3,132,208 | 5/1964 | Dymski et al. ............................ 179/1 |
| 3,160,708 | 12/1964 | Dymski et al. ............................ 179/1 |
| 3,182,129 | 5/1965 | Clark et al. ................................ 179/1 |
| 3,227,836 | 1/1966 | Renwick, Sr. ......................... 200/61.58 |
| 3,233,041 | 2/1966 | Croslin ....................................... 179/1 |
| 3,247,324 | 4/1966 | Cefaly et al. .............................. 179/1 |
| 3,396,241 | 8/1968 | Anderson et al. .......................... 179/1 |
| 3,455,293 | 7/1969 | Bethune ................................. 128/2.05 |
| 3,525,810 | 8/1970 | Adler ......................................... 179/1 |
| 3,539,724 | 11/1970 | Keesee ...................................... 179/1 |
| 3,665,087 | 5/1972 | Poylo ......................................... 35/17 |
| 3,667,569 | 6/1972 | Mackey et al. .......................... 181/131 |
| 3,746,124 | 7/1973 | Wilson et al. .......................... 181/131 |
| 3,762,397 | 10/1973 | Cage ................................. 128/2.05 S |
| 3,790,713 | 2/1974 | Andries ...................................... 179/1 |
| 3,846,585 | 11/1974 | Slosberg et al. ............................ 179/1 |
| 3,858,005 | 12/1974 | Marshall et al. ............................ 179/1 |
| 3,862,379 | 1/1975 | Pless ....................................... 179/167 |
| 3,906,160 | 9/1975 | Nakamura et al. ................. 179/15 BT |
| 3,989,895 | 11/1976 | O'Daniel .................................... 179/1 |
| 4,007,806 | 2/1977 | Nobles, Jr. .............................. 181/131 |
| 4,048,444 | 9/1977 | Glampapa .................................. 179/1 |
| 4,071,694 | 1/1978 | Pfeiffer ................................. 179/1 ST |
| 4,072,822 | 2/1978 | Yamada ................................... 179/1.5 |
| 4,170,717 | 10/1979 | Walshe ................................. 179/1 ST |
| 4,184,493 | 1/1980 | Langer et al. ....................... 128/419 D |
| 4,200,169 | 4/1980 | MacDonald, III et al. ............ 181/131 |
| 4,220,160 | 9/1980 | Kimball et al. ......................... 128/715 |
| 4,254,302 | 3/1981 | Walshe ................................. 179/1 ST |
| 4,270,627 | 6/1981 | Hill ........................................ 181/131 |

(List continued on next page.)

FOREIGN PATENT DOCUMENTS

| | | | |
|---|---|---|---|
| A-0 454 931 | 11/1991 | European Pat. Off. .......... A61B 7/04 |
| A-91 07 532 | 6/1992 | Germany ......................... A61B 7/04 |

*Primary Examiner*—Forester W. Isen
*Assistant Examiner*—Xu Mei
*Attorney, Agent, or Firm*—Wolf, Greenfield, Sacks, P.C.; James H. Morris

[57] ABSTRACT

An electronic stethoscope having several modes of operation to process acoustic signals to provide filtered signals useful for diagnosis. In one mode of operation the stethoscope substantially provides only acoustic signals generated by biological activity of the heart. In another mode of operation, the acoustic stethoscope substantially provides only acoustic signals generated by biological activity of the lungs. In another mode of operation, the electronic stethoscope disproportionately amplifies abnormal heart sounds and normal heart sounds to enhance diagnosis of heart abnormalities. The electronic stethoscope is operated in a manner similar to a conventional acoustic stethoscope and has similar spectral characteristics, thus allowing a user with acoustic stethoscope experience to easily use the electronic stethoscope.

15 Claims, 28 Drawing Sheets

U.S. PATENT DOCUMENTS

| | | | |
|---|---|---|---|
| 4,299,303 | 11/1981 | Clark | 181/131 |
| 4,306,567 | 12/1981 | Krasner | 128/671 |
| 4,362,164 | 12/1982 | Little et al. | 128/639 |
| 4,377,727 | 3/1983 | Schwalbach | 179/1 |
| 4,387,784 | 6/1983 | Hill | 181/131 |
| 4,424,815 | 1/1984 | Kuntz | 128/715 |
| 4,436,096 | 3/1984 | Dyck et al. | 128/689 |
| 4,438,772 | 3/1984 | Slavin | 128/715 |
| 4,440,258 | 4/1984 | Packard | 181/131 |
| 4,498,188 | 2/1985 | Hofer | 381/67 |
| 4,502,562 | 3/1985 | Nelson | 181/131 |
| 4,506,678 | 3/1985 | Russell et al. | 128/723 |
| 4,528,689 | 7/1985 | Katz | 381/67 |
| 4,528,690 | 7/1985 | Sedgwick | 381/67 |
| 4,534,058 | 8/1985 | Hower | 381/67 |
| 4,594,731 | 6/1986 | Lewkowicz | 381/67 |
| 4,598,417 | 7/1986 | Deno | 381/67 |
| 4,618,986 | 10/1986 | Hower | 381/67 |
| 4,619,268 | 10/1986 | Uphold et al. | 128/671 |
| 4,633,971 | 1/1987 | Robbins | 181/131 |
| 4,649,930 | 3/1987 | Groch et al. | 128/695 |
| 4,672,975 | 6/1987 | Sirota | 128/715 |
| 4,672,977 | 6/1987 | Kroll | 128/715 |
| 4,720,866 | 1/1988 | Elias et al. | 381/67 |
| 4,723,555 | 2/1988 | Shue | 128/715 |
| 4,731,849 | 3/1988 | Bloomfield, III | 381/67 |
| 4,763,663 | 8/1988 | Uphold et al. | 128/671 |
| 4,770,189 | 9/1988 | Shyu | 128/773 |
| 4,777,961 | 10/1988 | Saltzman | 128/715 |
| 4,783,813 | 11/1988 | Kempka | 381/67 |
| 4,783,814 | 11/1988 | Foley | 381/67 |
| 4,792,145 | 12/1988 | Eisenberg et al. | 128/715 |
| 4,795,069 | 1/1989 | Ferrill | D24/134 |
| 4,821,327 | 4/1989 | Furugard et al. | 381/67 |
| 4,852,684 | 8/1989 | Packard | 181/131 |
| 4,878,501 | 11/1989 | Shue | 128/715 |
| 4,903,794 | 2/1990 | Klippert et al. | 181/131 |
| 4,913,259 | 4/1990 | Packard | 181/131 |
| 4,940,023 | 7/1990 | Shue | 128/715 |
| 4,967,760 | 11/1990 | Bennett, Jr. et al. | 128/715 |
| 4,972,841 | 11/1990 | Iguchi | 128/715 |
| 5,003,605 | 3/1991 | Phillipps et al. | 381/67 |
| 5,010,889 | 4/1991 | Bredesen et al. | 128/715 |
| 5,022,415 | 6/1991 | Hök et al. | 128/715 |
| 5,025,809 | 6/1991 | Johnson et al. | 128/715 |
| 5,027,824 | 7/1991 | Dougherty et al. | 128/702 |
| 5,027,825 | 7/1991 | Phelps, Sr. et al. | 128/715 |
| 5,165,417 | 11/1992 | Murphy, Jr. | 128/716 |
| 5,204,500 | 4/1993 | Dufresne et al. | 181/131 |
| 5,213,108 | 5/1993 | Bredesen et al. | 128/715 |
| 5,218,969 | 6/1993 | Bredesen et al. | 128/710 |
| 5,301,679 | 4/1994 | Taylor | 128/773 |
| 5,347,583 | 9/1994 | Dieken et al. | 381/67 |
| 5,367,575 | 11/1994 | Dieken et al. | 381/67 |
| 5,466,898 | 11/1995 | Gilbert et al. | 181/131 |
| 5,557,681 | 9/1996 | Thomasson | 381/67 |
| 5,561,275 | 10/1996 | Savage et al. | 381/67 |
| 5,663,533 | 9/1997 | Judge | 181/131 |
| 5,687,738 | 11/1997 | Shapiro et al. | 128/715 |
| 5,708,725 | 1/1998 | Ito | 381/183 |
| 5,774,563 | 6/1998 | DesLauriers et al. | 381/67 |
| 5,832,093 | 11/1998 | Berstein et al. | 381/67 |

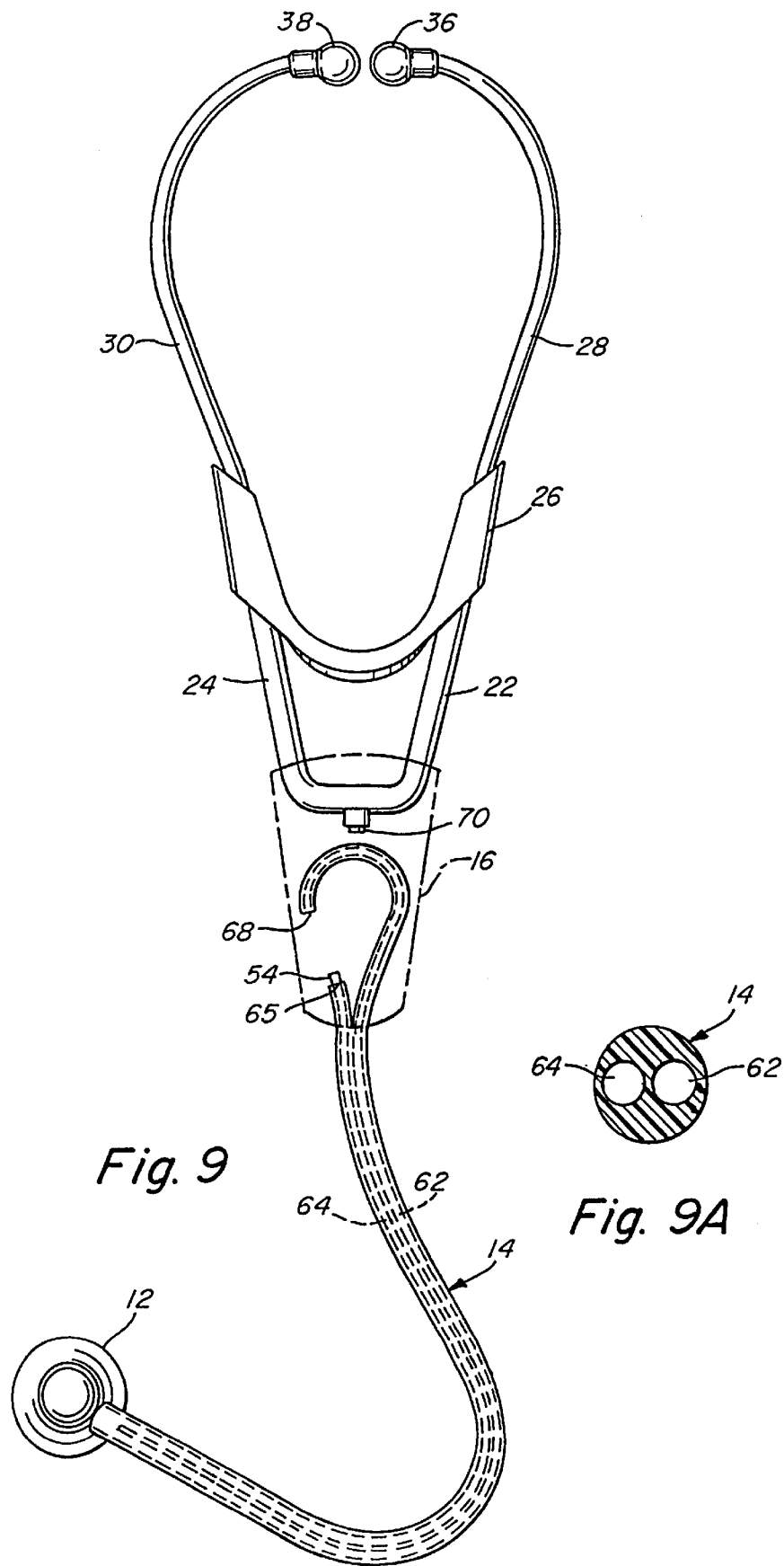

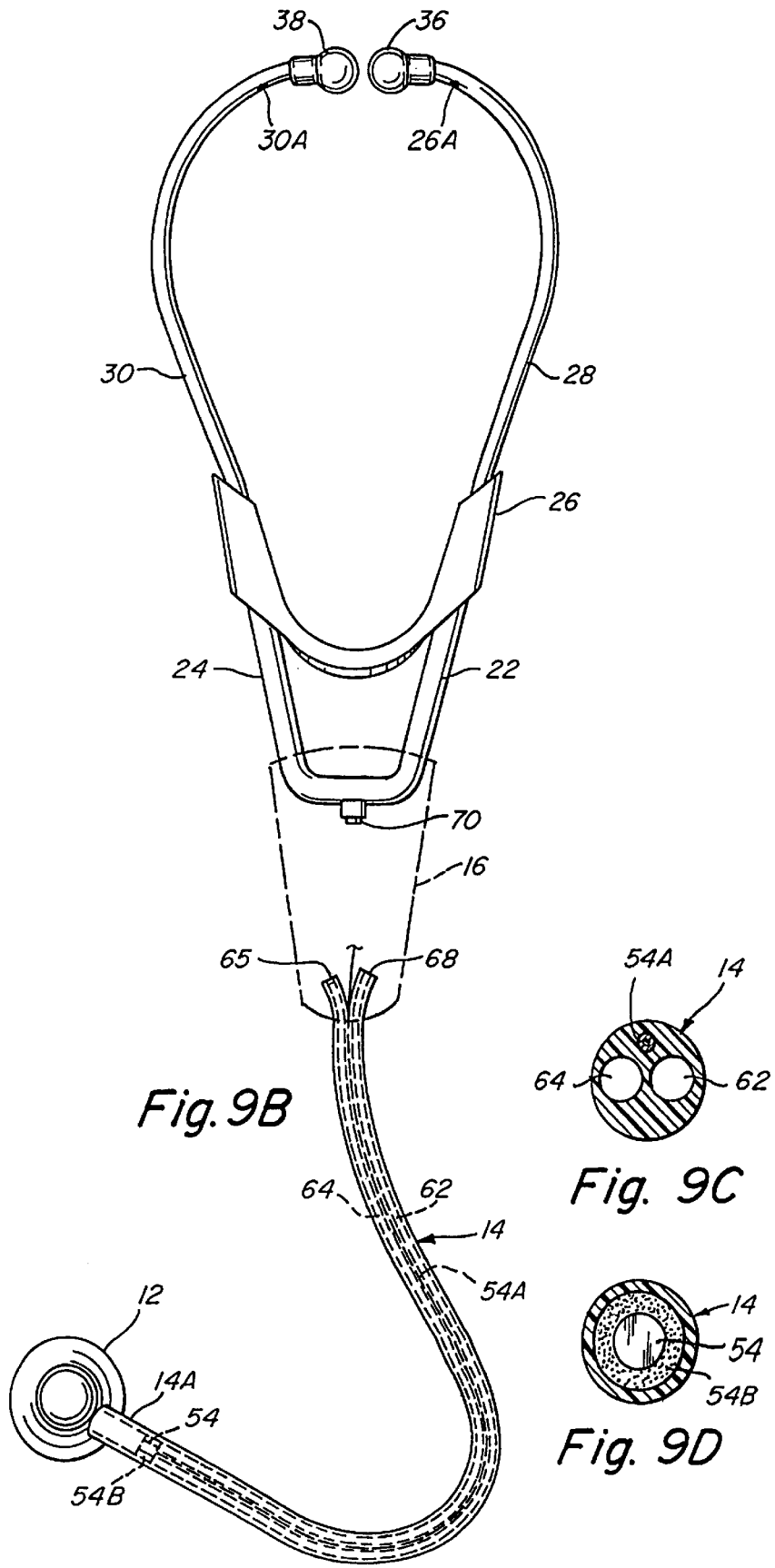

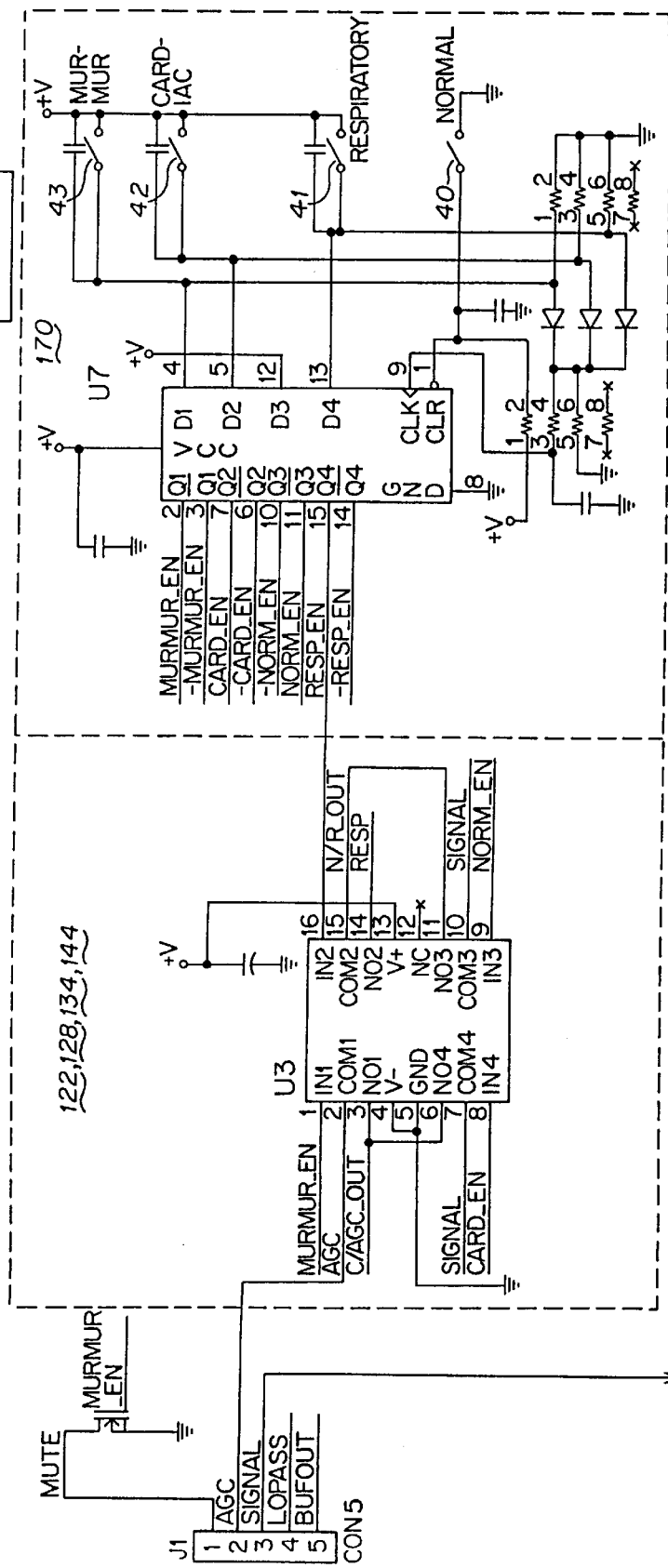

ELECTRONIC STETHOSCOPE

CROSS REFERENCE TO RELATED APPLICATIONS

This application is a division of application Ser. No. 08/685,451, filed Jul. 19, 1996, entitled ELECTRONIC STETHOSCOPE which in turn is a continuation-in-part of application Ser. No. 08/505,601, filed Jul. 21, 1995 now abandoned, entitled ELECTRONIC STETHOSCOPE, which prior applications are incorporated herein by reference.

BACKGROUND OF THE INVENTION

1. Field of the Invention

The present invention relates generally to stethoscopes used for diagnostic purposes. More particularly, the present invention relates to electronic stethoscopes and methods for processing signals in electronic stethoscopes for diagnostic purposes.

2. Discussion of the Related Art

Electronic stethoscopes are known in the art. Examples of electronic stethoscopes may be seen in U.S. Pat. Nos. 3,247,324, 4,071,694, 4,170,717, 4,254,302, 4,438,772, 4,528,690, 4,534,058, and 4,618,986.

Despite the availability of electronic stethoscopes, they do not appear to be widely used by medical personnel, such as doctors, nurses, and emergency medical technicians. Although the reasons for this lack of acceptance are not completely clear, one problem with some presently available electronic stethoscopes may be that they do not reproduce acoustic signals resulting from the operation of various body organs in a manner that is familiar to a trained user. Other problems with some presently available electronic stethoscopes are that they consume too much power, weigh too much, are too large, or require a user to change the manner in which the stethoscope is used as compared to a conventional acoustic stethoscope.

Medical personnel learn the art of auscultation primarily through the use of an acoustic stethoscope and are trained to hear normal and abnormal heart and lung sounds based on their specific acoustic qualities and their timing relative to other biological sounds. Acoustic stethoscopes thus have particular characteristics whose effect upon the acoustic signals heard by the medical personnel become familiar and are relied upon for diagnosis. Some conventional electronic stethoscopes do not reproduce heart and lung sounds with the same spectral characteristics as acoustic stethoscopes.

Therefore, an object of the present invention is to provide an electronic stethoscope that overcomes at least the above-discussed disadvantages.

Another object of the present invention is to provide a method for processing acoustic signals generated by biological activity to provide enhanced diagnostic information.

SUMMARY OF THE INVENTION

The present invention overcomes the disadvantages of the prior art by providing an electronic stethoscope that closely resembles a typical acoustic stethoscope. The present invention feels and operates, to a user, like an acoustic stethoscope, but with enhanced performance characteristics.

In one embodiment, the invention includes an electronic stethoscope having a first transducer for converting acoustic signals into electronic signals, a processing section, having input coupled to an output of the first transducer, for processing the electronic signals to provide selected electronic signals representative of only selected ones of the acoustic signals, and a second transducer, coupled to an output of the processing section, for converting the selected electronic signals into acoustic signals. The electronic stethoscope may include a bandpass filter between the first transducer and the processing section to filter out inaudible signals. The bandpass filter may also be used to filter out sounds that are outside the frequency range of heart and lung sounds.

The electronic stethoscope may have several modes of operation. In a "normal" operational mode, the stethoscope transmits the electronic signals from the first transducer through the processing section to the second transducer substantially unchanged. This mode of operation is designed to mimic the operation of an acoustic stethoscope so that the acoustic signals heard by the user have substantially the same spectral characteristics as they would have if being processed by an acoustic stethoscope but with the additional capability of being able to adjust the volume of the acoustic signals. In this mode, a user can hear, among other sounds, sounds generated by vascular activity or blood flow. Within this disclosure, the term "normal", when referring to the operation of the stethoscope, is meant to refer to the acoustic response or spectral characteristics of a typical conventional acoustic stethoscope but without any response to harmonics outside the frequency range of heart and lung sounds. In a "respiratory" operational mode, the electronic signals from the bandpass filter are filtered by a high pass filter before being transmitted to the second transducer. This filtering operation substantially filters out electronic signals corresponding to acoustic signals generated by biological activity other than the lungs so that the stethoscope user hears substantially only those sounds generated by lung activity. The high pass filter may have a corner frequency in the range of 100 to 300 Hz.

The electronic stethoscope may also have a "cardiac" operational mode in which the electronic signals from the bandpass filter are filtered by a low pass filter before being transmitted to the second transducer. This mode of operation substantially filters out electronic signals corresponding to acoustic signals generated by biological activity other than the heart so that the stethoscope user hears substantially only sounds generated by heart activity. The low pass filter may have a corner frequency in the range of 400 to 600 Hz.

The electronic stethoscope may also have a "murmur enhancement" operational mode in which the electronic signals from the bandpass filter are processed by an automatic gain control circuit and then transmitted to the low pass filter. The murmur enhancement mode allows the stethoscope to disproportionately amplify, relative to heart sounds generated by normal cardiac activity (i.e., for example, so called "dominant" or "first" and "second" heart sounds), heart sounds generated by abnormal cardiac activity (i.e., for example, murmur sounds) while at the same time not amplifying the volume of the normal cardiac activity. This allows the user to more clearly determine the relationship between the abnormal heart sound and the normal heart sound. This has the effect of amplifying the low level murmur activity without significantly amplifying the normal cardiac activity. This mode of operation also allows a user to hear heart murmurs more clearly. This mode of operation also allows a user to hear heart sounds that may be inaudible or difficult to hear using a typical acoustic stethoscope. In one embodiment, the automatic gain control circuit has a response time constant in the range of 5 to 100 ms.

The various operational modes can be selected in real time without the need for moving the chestpiece.

In other embodiments, the electronic stethoscope includes a transceiver, coupled between the bandpass filter and the processing system for transmitting electronic signals from the bandpass filter to a remote device and/or receiving electronic signals from a remote device to be processed by the processing system. In this way, the electronic stethoscope can transmit the entire spectrum of electronic signals being detected to another stethoscope or multiple stethoscopes so that more than one user can participate in the diagnostic process. In the same manner the electronic stethoscope can receive electronic signals so that a user can hear these received signals and individually, independently, and simultaneously process the received signals. This allows, among other things, real-time transmission and reception of the electronic signals, so that several users can participate in the diagnostic process simultaneously.

Another feature of the electronic stethoscope of the invention is a switch for controlling power including a first pole of the switch attached to a first binaural in the pair of binaurals of the stethoscope and a second pole of the switch attached to a second binaural in the pair of binaurals. A spring is mechanically coupled to each binaural and, in a rest position, urges the first and second binaurals together. When the closing force of the spring is overcome and the binaurals are separated by a predetermined distance, the first pole and the second pole make electrical contact to supply electrical power to the signal processing circuitry. Upon release of the binaurals, the spring urges the binaurals together and the first pole and second pole are separated to remove electrical power from the signal processing circuitry. This provides a convenient and familiar way of operating the electronic stethoscope that does not require any new activity or steps compared to an acoustic stethoscope that does not have to be turned on or off.

The overall operation of the electronic stethoscope is characterized by filtering of acoustic signals generated by human biological activity, such as respiratory and cardiac activity, to substantially isolate a selected acoustic signal or set of acoustic signals generated by a particular organ from the acoustic signals. The electronic stethoscope performs this function by converting acoustic signals generated by human biological activity into electronic signals, selectively filtering the electronic signals to provide a filtered electronic signal that contains substantially only electronic signals representative of acoustic signals generated by a particular organ, and converting the filtered electronic signal into an audible acoustic signal. In one embodiment, the step of selectively filtering includes high pass filtering the electronic signals so that the filtered electronic signal contains substantially only electronic signals representative of acoustic signals generated by lung activity. In another embodiment, the step of selectively filtering includes the step of low pass filtering the electronic signal so that the filtered electronic signal contains substantially only electronic signals representative of acoustic signals generated by cardiac activity. In another embodiment, the step of selectively filtering includes the steps of disproportionately amplifying the electronic signals and low pass filtering the electronic signals so that the filtered electronic signal contains substantially only electronic signals representative of normal cardiac sounds and amplified abnormal cardiac sounds.

Another feature of the invention is the shape of the binaurals that carry the acoustic signals to the user's ears. In the present invention, the binaurals are configured so that they conform to the user's body so as to hang comfortably around the user's neck in a "stand-by" position. To accomplish this, each of the first binaural and the second binaural has a first curve that substantially follows a shape of a human body from a neck region to a chest region and a second curve that substantially follows a shape of a human body from a base of the neck region to a shoulder region. Each binaural also has a third curve in the region of the earpieces and is rotated so that the earpieces are substantially aligned with the user's ear canals when the stethoscope is placed in its "in-use" position.

The electronic stethoscope of the invention may be used to listen to biological activity (e.g., organ sounds) of humans as well as animals.

The features and advantages of the present invention will be more readily understood and apparent from the following detailed description of the invention, which should be read in conjunction with the accompanying drawings, and from the claims which are appended at the end of the detailed description.

BRIEF DESCRIPTION OF THE DRAWINGS

In the drawings, which are incorporated herein by reference and which like elements have been given like reference characters.

FIGS. 9 and 9A illustrate a second acoustic topology that may be used in the electronic stethoscope of FIG. 1;

FIGS. 9B, 9C, and 9D illustrate a third acoustic topology that may be used in the electronic stethoscope of FIG. 1;

DETAILED DESCRIPTION

For purposes of illustration only, and not to limit generality, the present invention will now be explained with reference to an electronic stethoscope for use in heart and lung diagnosis in humans. Specific ranges of operation and frequencies will be discussed in this context. One skilled in the art will appreciate, however, that the present invention is not so limited and that by changing the operational frequencies and other stethoscope parameters, the present invention may be used to diagnose other types of human biological activity as well as biological activity in infants, children, animals, and so on.

Figures 1, 1A:
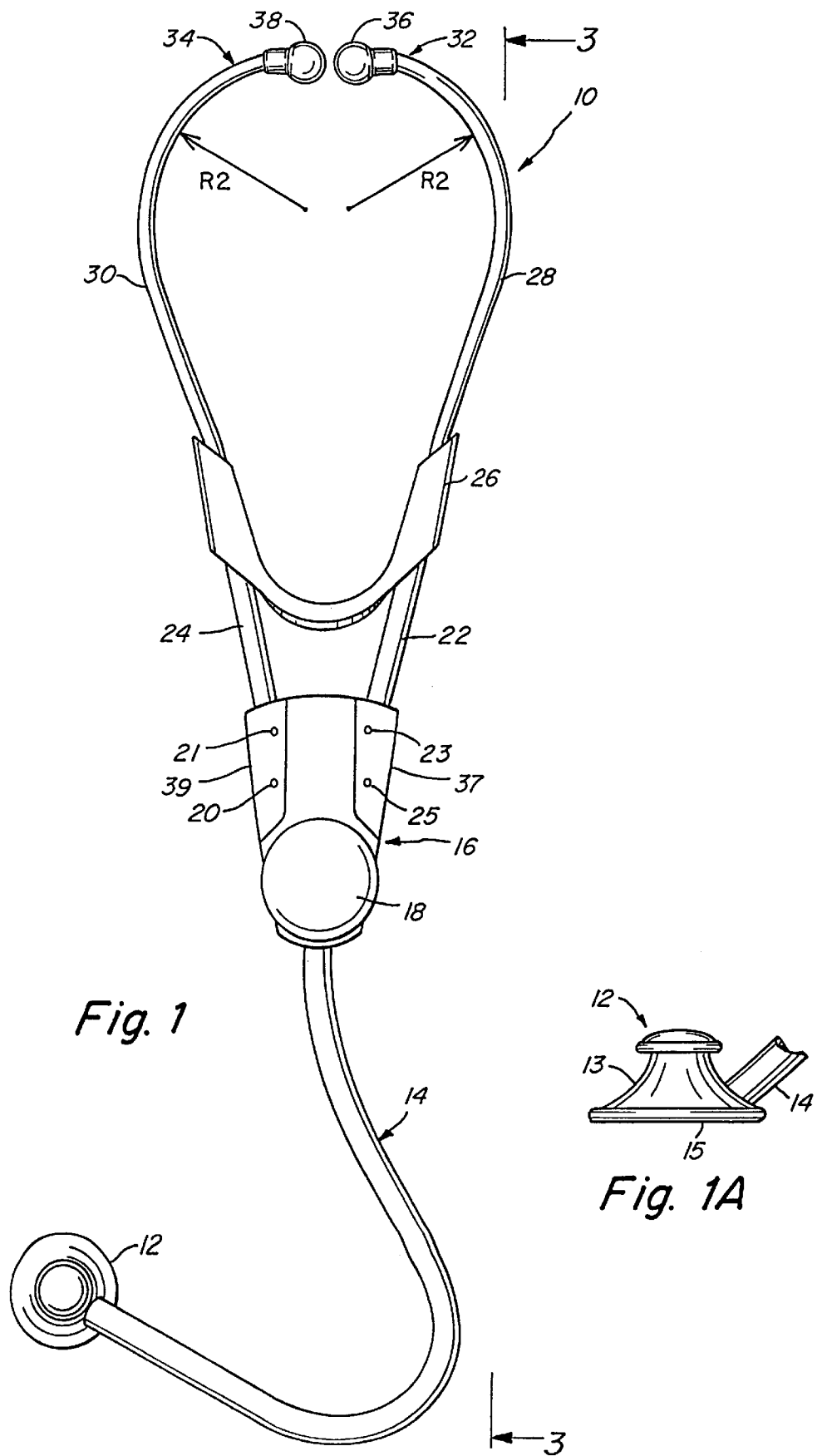
FIG. 1 is an overall view of the electronic stethoscope of the invention.
FIG. 1A is a side view of the chestpiece of the electronic stethoscope of the invention.
Figure 2:
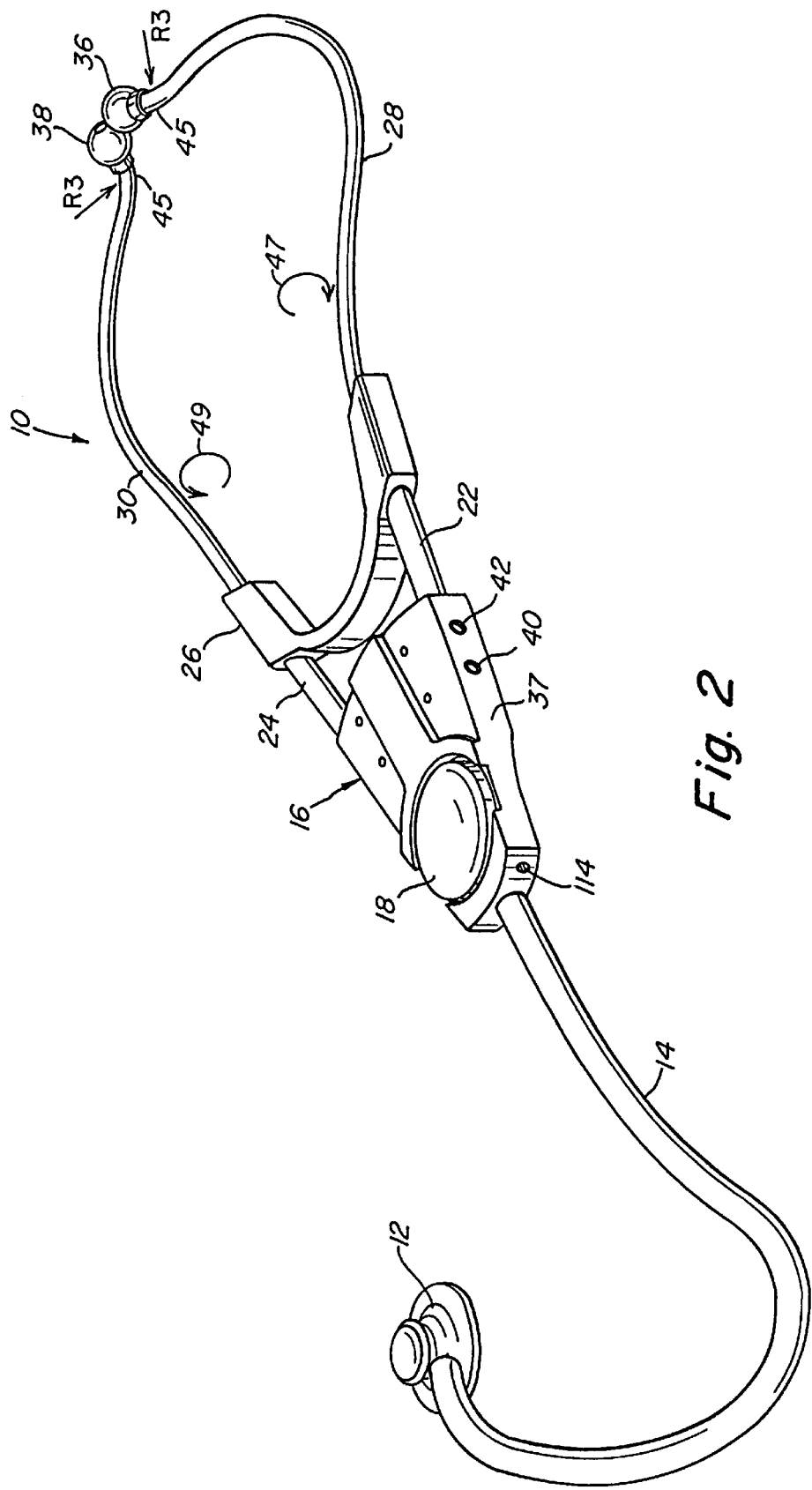
FIG. 2 is an overall perspective view of the electronic stethoscope of FIG. 1.
Figure 3:
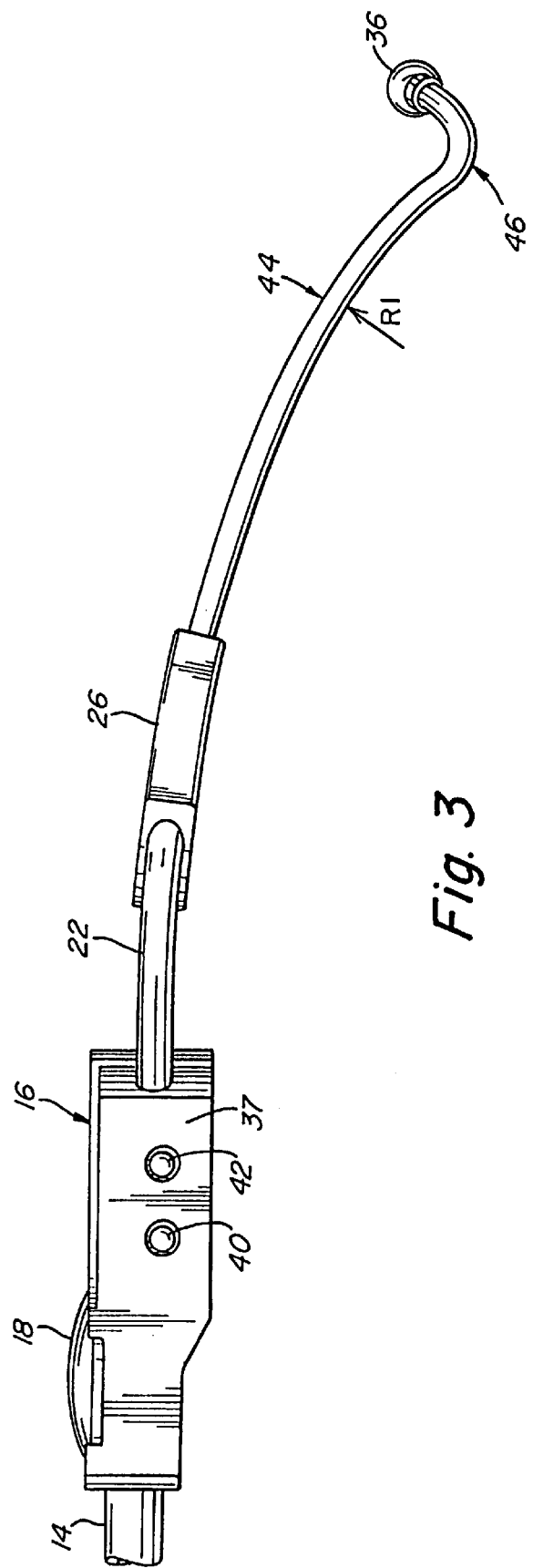
FIG. 3 is a side view of FIG. 1 along line 3—3 illustrating, among other features, the shape of the binaurals.
Figure 4:
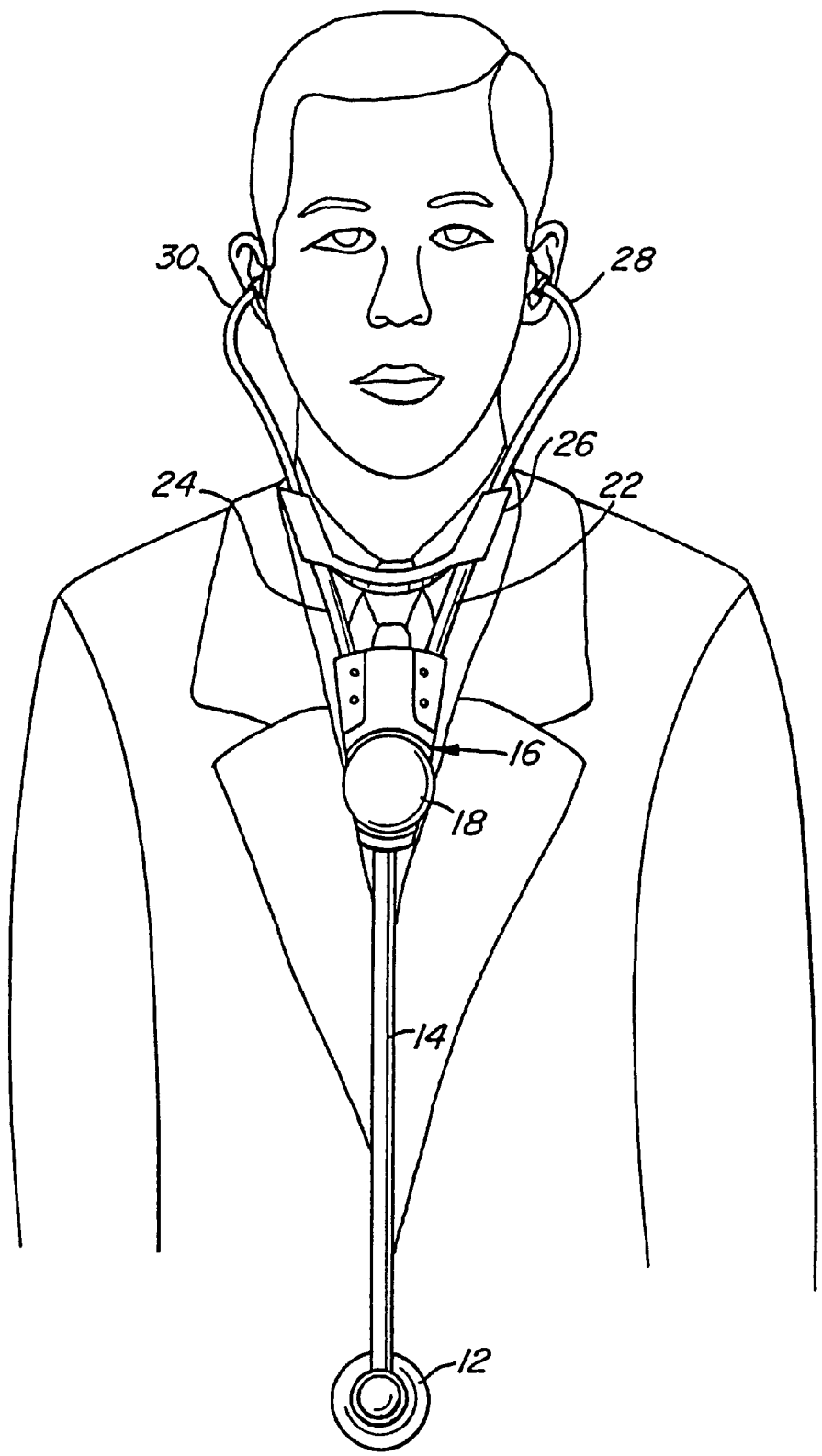
FIGS. 4, 5, 6, and 7 illustrate the electronic stethoscope of FIG. 1 in rest and in use positions.

Reference is now made to FIGS. 1, 2, and 3 which Figures illustrate the overall configuration of the electronic stethoscope of the invention. The electronic stethoscope 10 includes a chestpiece 12 that is used to detect and convert biological activity of particular organs into acoustic pressure waves (i.e., acoustic signals). The acoustic signals are transmitted through a flexible acoustic tube 14. An electronics housing 16 contains circuitry that allows the stethoscope to provide a number of diagnostic functions, to be described in more detail hereinafter. A knob 18 is located on electronics housing 16 and allows a user of the stethoscope to easily adjust the volume of the acoustic signals produced by the electronic circuitry. Also on the housing are visual indicators 20, 21, 23, and 25 that illuminate depending on the particular mode of operation that the stethoscope is in. Visual indicators 20, 21, 23, and 25 may be light emitting diodes. Attached to electronics housing 16 are first and second flexible acoustic conduits 22 and 24. As will be explained in more detail hereinafter, in one embodiment of the invention, acoustic conduits 22 and 24 transmit acoustic pressure waves from chestpiece 12. In another embodiment of the invention, acoustic conduits 22 and 24 transmit acoustic signals resulting from processing by the electronics contained within electronics housing 16.

Acoustic conduits 22 and 24 are coupled to a spring and switch housing 26. As will be explained in more detail hereinafter, spring and switch housing 26 contains a switch for controlling the application of electrical power to the electronic circuitry in electronics housing 16.

Acoustic conduits 22 and 24 are respectively coupled, through spring and switch housing 26, to first and second hollow binaurals 28 and 30. At the ends 32, 34 of the binaurals are respectively located first and second earpieces 36, 38. Earpieces 36 and 38 are typically rubber, plastic, or foam pads used to cushion contact with the user's ears. The binaurals 28 and 30 may be aluminum alloy.

Chestpiece 12 has a housing 13 constructed of aluminum alloy resulting in a chestpiece lighter in weight and which we have found to provide greater patient comfort than the stainless steel used in typical acoustic stethoscopes. The greater patient comfort comes from the fact that the aluminum alloy has high thermal conductivity and the aluminum alloy chestpiece has low thermal mass. Thus, the chestpiece is more likely to be warmed by the user's hand prior to coming in contact with the patient's skin, resulting in minimal thermal shock to the patient. The chestpiece uses a diaphragm 15 constructed of polycarbonate. Unlike typical acoustic stethoscopes, the chestpiece in the electronic stethoscope of the invention uses only a single diaphragm and a bell is unnecessary. Adapters or different sized chestpieces tuned to respond to different frequency ranges are not required for different patients (e.g., infants vs. adults) because any necessary modification of the spectral characteristics of the stethoscope can be carried out electronically.

Buttons 40 and 42 on side 37 as well as two other buttons on side 39 are used to switch the electronic stethoscope from one mode of operation to another. One of the visual indicators 20, 21, 23, or 25 is illuminated in response to activation of the mode buttons.

Figure 5:
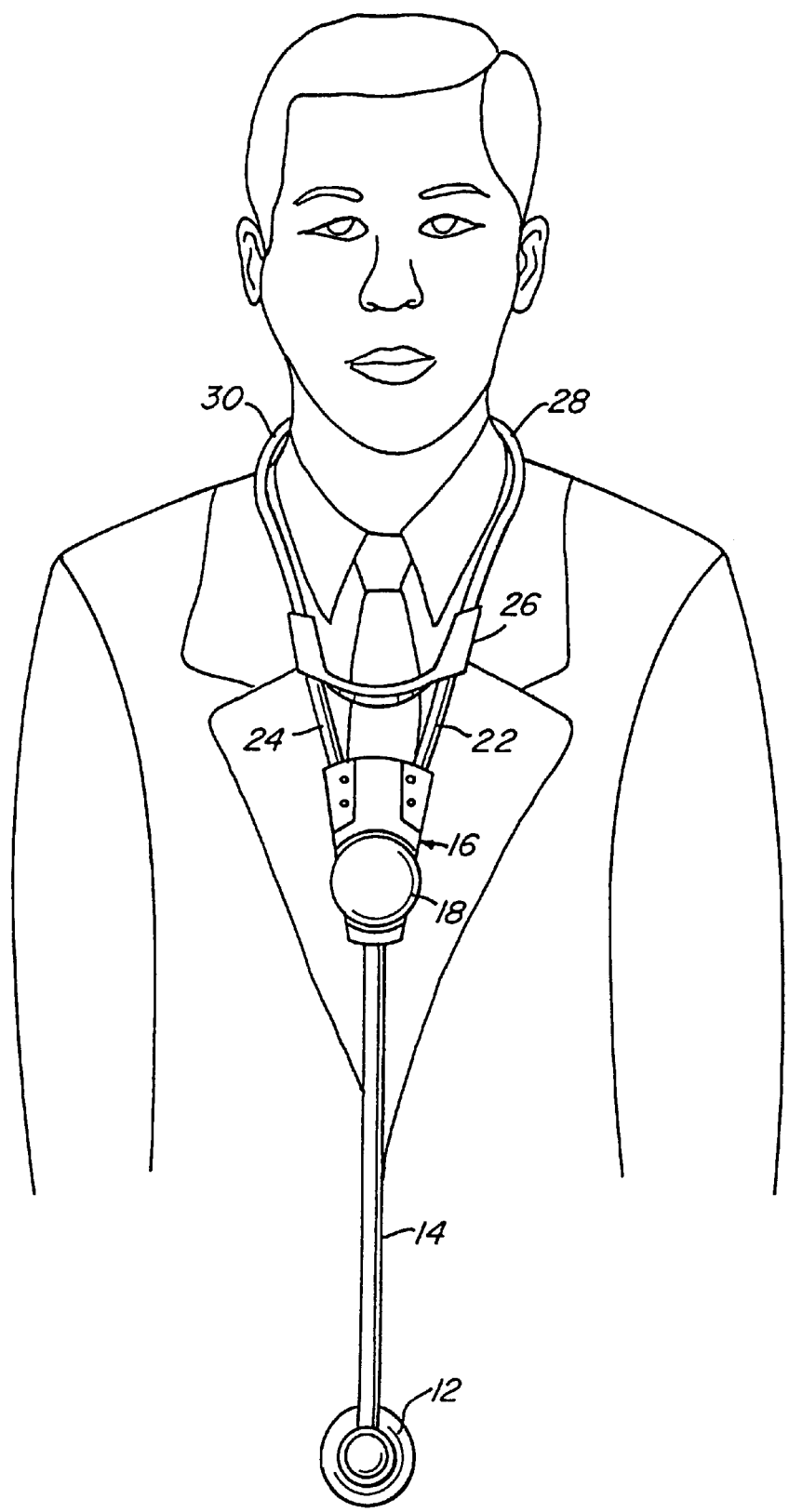
Figure 6:
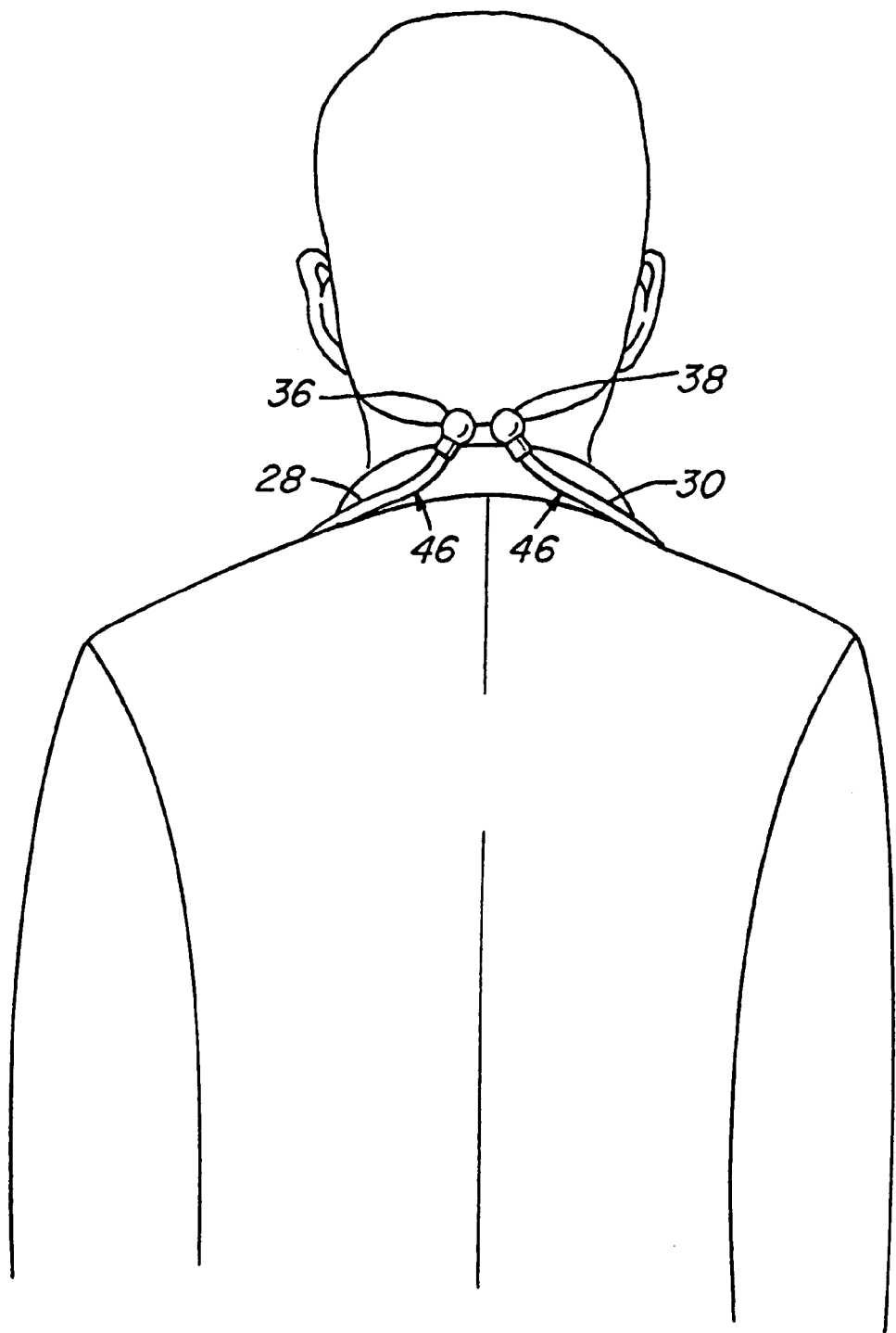
Figure 7:
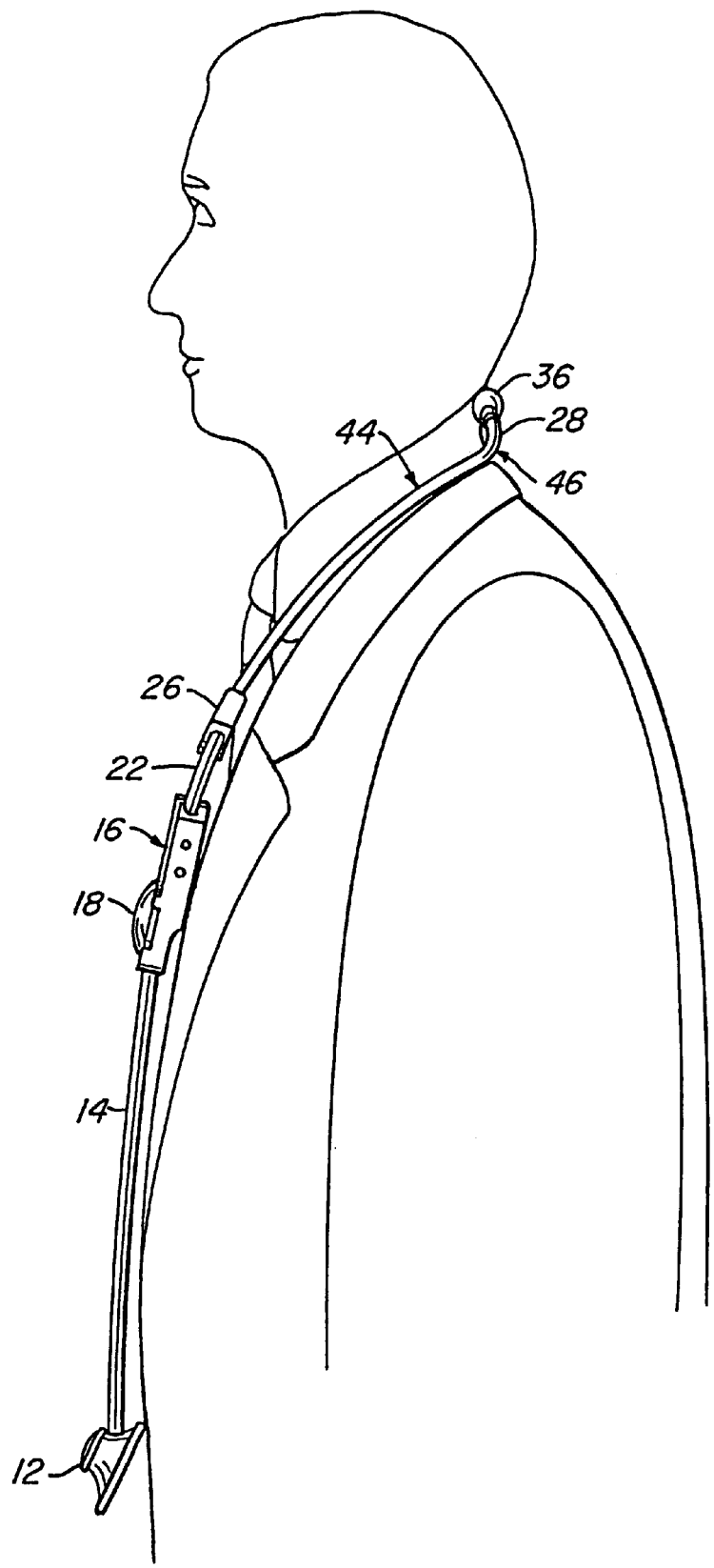

A feature of the electronic stethoscope of the present invention is the configuration of the binaurals. In many acoustic stethoscopes, the binaurals lie in a single plane and therefore do not fit the natural curves of the body when stored around the user's neck. Many acoustic stethoscopes actually pinch the user's neck when stored in this common standby position. By contrast, as shown particularly in FIG. 3, the binaurals of the electronic stethoscope of the invention include a first curved portion 44 that is angled so as to lie naturally and comfortably on the user's neck, shoulders and upper chest with electronics housing 16 lying against the user's chest. The binaurals also include a second curved portion 46 that allows the binaurals (and the entire stethoscope) to hang comfortably around the user's neck. FIGS. 4, 5, 6, and 7 illustrate the electronic stethoscope of the invention in both its "in use" position (FIG. 4) and its "standby" position (FIGS. 5, 6, and 7). As can be seen from the figures, one of the reasons that the stethoscope fits comfortably around a user's neck is due to the fact that curves 44 and 46 are compound and pass through multiple planes. In one embodiment, curve 44 has approximately a radius R1 in the range of 3 to 4 inches and curve 46 has approximately a radius R2 in the range of 2 to 3 inches. In a preferred embodiment, radius R1 has approximately a 3.6 inch radius and radius R2 has approximately a 2.5 inch radius. We have found that this combination of radii advantageously provide a stethoscope that fits a wide range of users comfortably. The shape of the binaurals allows the stethoscope to lie comfortably flat against the user's chest and around the neck. The stethoscope is easily and quickly shifted from its "standby" position to its "in use" position.

An additional curve 45 is also provided having a radius R3 in the range of 1.25 to 1.75 inches. In a preferred embodiment, radius R3 has approximately a 1.5 inch radius. In addition, the first and second binaurals are respectively rotated in the direction of arrows 47, 49 so that earpieces 36, 38 are angled upwards as shown in FIGS. 3 and 6. This allows earpieces 36, 38 to be substantially aligned with the user's ear canals so as to enhance sound transmission in the "in-use" position.

Figure 8:
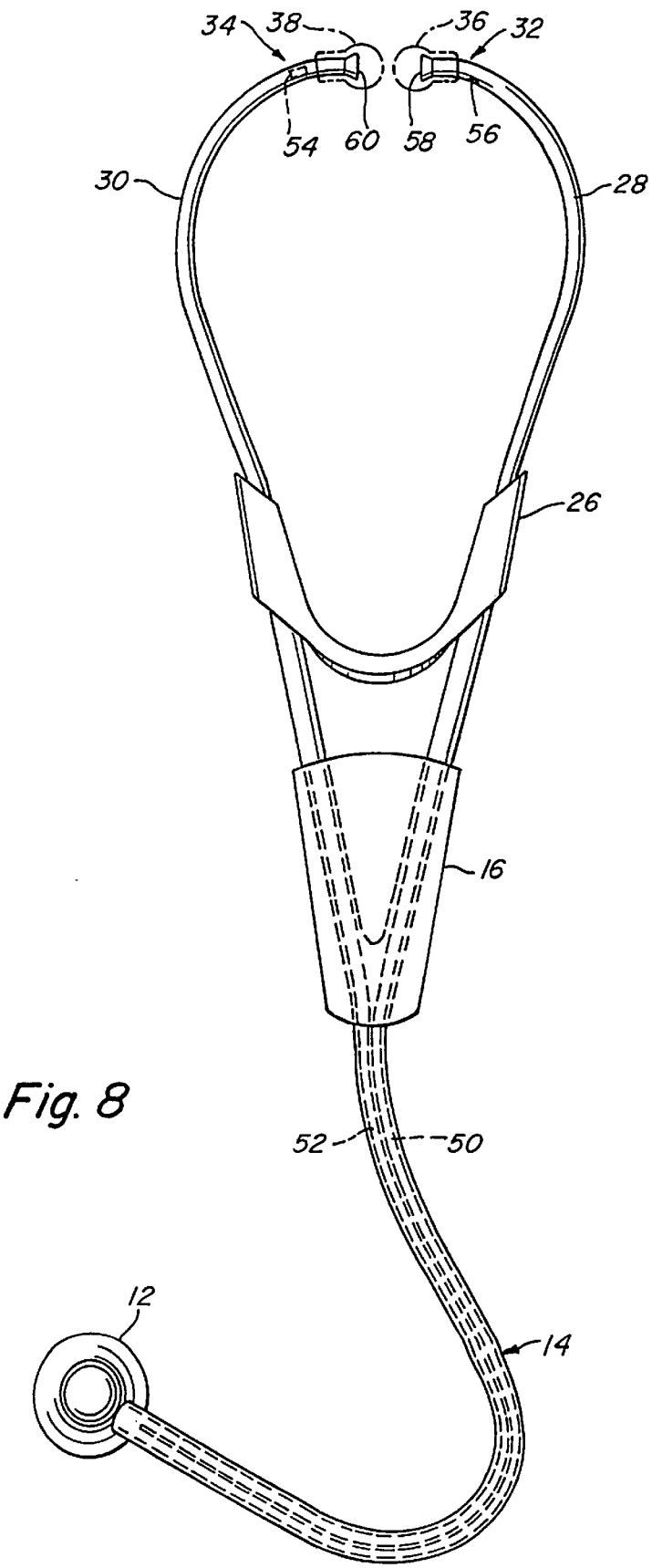
FIG. 8 illustrates a first acoustic topology that may be used in the electronic stethoscope of FIG. 1.

Reference is now made to FIG. 8, which figure illustrates a first acoustic topology of the electronic stethoscope. The acoustic topology should be chosen so as to closely replicate the normal performance of an acoustic stethoscope so as to make the transition from using an acoustic stethoscope to the electronic stethoscope intuitive.

In the acoustic topology illustrated in FIG. 8, acoustic signals picked up by the diaphragm in the chestpiece 12 are routed to the flexible acoustic tube 14. Flexible acoustic tube 14 encloses two parallel acoustic conduits 50, 52. Acoustic conduit 50 continues through electronics housing 16, spring and switch housing 26 and continues through the first binaural 32. The second acoustic conduit 52 continues through electronics housing 16, spring and switch housing 26, and binaural 34. A microphone 54 is located near the end 34 of the second binaural 30. Microphone 54 picks up the sounds transmitted through the chestpiece 12 and acoustic conduit 52 and converts the acoustic signals into electronic signals that are processed by the electronic circuitry located in the electronics housing 16. A vent 56 is provided at the end 32 of binaural 28 to allow excess air pressure to escape that may otherwise result in distortion caused by excess air pressure on the microphone. Once the electronic signals have been processed by the electronic circuitry in electronics housing 16, these signals are reconverted to acoustic signals using miniature headphones 58 and 60 located in binaurals 28 and 30, respectively. The first and second earpieces 36, 38 form a seal with the user's ear canals to block ambient sounds and enhance the transmission of very low frequency sounds through the stethoscope. Locating the microphone 54 near the end of the binaural allows the full resonant chamber created by acoustic conduits 50 and 52 to enhance the intensity of the low frequencies picked up by the chestpiece before these sounds are converted into electronic signals.

Reference is now made to FIG. 9, which figure illustrates a second acoustic topology that may be used in the electronic stethoscope of the invention. In the second acoustic topology, sounds picked up by chestpiece 12 are transmitted through acoustic conduits 62, 64 in flexible acoustic tube 14. As shown in FIG. 9A, the flexible acoustic tube 14 encloses two parallel acoustic conduits. This design has been found to reduce extraneous noise that could be picked up between the chestpiece and microphone transducer or noise that could be generated by contact with flexible acoustic tube 14.

Both acoustic conduits 62 and 64 terminate inside electronics housing 16. Acoustic conduit 64 is acoustically coupled to microphone 54 inside electronics housing 16. Microphone 54 may be an electret condenser microphone. The second acoustical conduit 62 is fully contained within electronics housing 16 and terminates with an open end 68. Acoustic conduit 62 is of a longer length. The length of acoustic conduit 62 and the length of acoustic conduit 64 in combination with the open end 68 of acoustic conduit 62 are selected to provide an acoustic chamber that imparts to the acoustic signals substantially the same tonal qualities as are provided by an acoustic stethoscope. This is advantageous because it helps the electronic stethoscope produce acoustic signals that have a familiar sound to a user. As with the first acoustic topology, the open end 68 of acoustical conduit 62 allows excess air pressure to escape so as to eliminate distortion in the acoustic signals detected by microphone 54. The combination of the lengths and the termination conditions of acoustic conduits 62 and 64 is chosen so as to form a resonant chamber that reproduces the sound characteristics of an acoustic stethoscope.

The microphone 54 picks up the sounds transmitted through the chestpiece 12 and flexible acoustic tube 14 and converts the acoustic signals into electronic signals. These electronic signals are then processed by the electronic circuitry contained within electronics housing 16. The processed electronic signals are then reconverted to acoustic signals using a single miniature speaker 70. Speaker 70 is acoustically coupled to the first and second flexible acoustic conduits 22 and 24 which are mechanically and acoustically coupled together within electronics housing 16. The acoustic signals are transmitted through first and second acoustic conduits 22 and 24 through first and second binaurals 28, 30 and earpieces 36, 38 to the user's ears.

The second topology illustrated in FIG. 9 provides several advantages. First, by mounting the microphone transducer and the speaker in electronics housing 16, fewer wires need to be run outside of the housing compared to the first acoustic topology illustrated in FIG. 8. This simplifies manufacturing. Additionally, keeping the microphone and the speaker inside electronics housing 16 reduces the risk of picking up stray radio frequency noise and of producing unwanted radio frequency emissions. Also, the second acoustic topology in which a single speaker feeds binaurals 28 and 30 preserves the conventional earpiece configuration of, for example, a typical acoustic stethoscope thus making the use of the electronic stethoscope more familiar to users. In addition, a single speaker coupled to binaurals 28 and 30 reduces amplification power requirements that in turn reduces the power consumption of the electronic circuitry contained in electronics housing 16 as well as reducing the number of parts needed. Also using a single speaker allows easier control and balance of the acoustic signals in the binaurals, since the same acoustic signal is provided to both binaurals through flexible acoustic conduits 22 and 24.

The acoustic topology illustrated in FIG. 9 also provides several advantages with respect to construction and manufacture of the stethoscope. In both the first acoustic topology in FIG. 8 and in a number of conventional acoustic stethoscopes, the combined acoustic path created by the combination of the chestpiece, tubing, and binaurals is of a fixed length and therefore has a predetermined resonant frequency. The resonant frequency and spectral characteristics are important factors in determining the normal response of an acoustic stethoscope. In order to make the overall length from chestpiece to earpiece practical for a user, and in order to preserve a useable resonant frequency, the overall length of an acoustic stethoscope for cardiac use is typically approximately 22 to 28 inches. These lengths result in resonant frequencies in the range of 120 Hz–155 Hz.

In the second topology illustrated in FIG. 9, the resonant frequency of the combined tube structure of the first and second acoustic conduits 62, 64 can be adjusted by increasing or decreasing the length of the second acoustic conduit 62 contained within electronics housing 16. As a result, the overall length of the electronic stethoscope of the invention can be varied over a relatively wide range (by changing the length of flexible acoustic tube 14) while maintaining a resonant frequency within the range of acoustic stethoscopes by increasing or decreasing the length of the second acoustic conduit (within electronics housing 16) to compensate for the increase or decrease in the overall length of the electronic stethoscope. Therefore, a desired resonant frequency can be held substantially constant over a broad range of overall stethoscope lengths. This allows the electronic stethoscope of the invention to maintain a resonant frequency comparable to a conventional acoustic stethoscope to provide "normal" sound characteristics even if the length of the electronic stethoscope is changed.

The electronic stethoscope of the invention, as illustrated in FIG. 9, uses an acoustic topology with a tube that has one closed end 65 and one open end 68. Sound is introduced near the middle of the tube (with the total tube length being the combination of the lengths of acoustic conduits 62 and 64) by the chestpiece diaphragm. This topology creates a standing pressure wave with a node at the closed end 65 and an anti-node at the open end 68. The wavelength of the a fundamental resonant frequency of this structure is four times the combined length of acoustic conduits 62 and 64.

The resonant frequency is approximately given by the following formula:

$$f = \frac{v}{4L}$$

where
v≈1132 ft/sec (speed of sound in air under typical working conditions for temperature and humidity)
L=overall tube length (ft)

In one embodiment of the invention, acoustical conduit 64 has a length of approximately twelve inches, acoustic conduit 62 has a length of approximately fifteen inches, and the acoustic path within the chestpiece 12 is approximately one inch. The resonant frequency of this total acoustic chamber formed by the chestpiece and the two acoustic conduits is approximately 121 Hz. As noted previously, the resonant frequency of a typical acoustic stethoscope designed for cardiac use is in the range of 120 Hz to 155 Hz. The lengths of the acoustic conduits in this embodiment have been found to provide a "normal" and familiar sound to trained users of acoustic stethoscopes. The resonant frequency is within the range of resonant frequencies in typical acoustic stethoscopes designed for cardiac use. The acoustic path length can be varied in order to adjust the resonant frequency and used in combination with variations in the parameters of the electronic processing circuitry contained within electronics housing 16 so as to optimize a particular stethoscope for detection of heart and/or lung sounds for specific applications such as infants, children, fetuses in the womb, animals of varying sizes, and prosthetic heart valves.

Reference is now made to FIGS. 9B, 9C, and 9D, which figures illustrate a third acoustic topology of the electronic stethoscope of the invention. The third acoustic topology is a variant of the topology illustrated in FIGS. 9 and 9A. In the third acoustic topology, the microphone 54 is suspended within the flexible acoustic tube 14 in proximity to the chestpiece 12. In one embodiment, the microphone is suspended approximately one inch from the end of the flexible acoustic tube 14 that mates to the chestpiece 12. The portion of flexible acoustic tube 14 containing microphone 54 contains a single acoustic conduit that is then split into acoustic conduits 64 and 62 just past microphone 54. Acoustic conduit 64 is sealed or closed at end 65. The microphone 54 is suspended preferably concentrically in the tube 14A by an energy dampening foam material 54B as illustrated in cross-section in FIG. 9D. Microphone 54 may be adhesively attached to foam 54B which is in turn adhesively attached to the inside of flexible acoustic tube 14. The energy dampening foam material 54B provides three functions simultaneously. First, foam material 54B provides air pressure relief by allowing the air column to pass by the microphone and through the foam material and into the open acoustic conduit 62. Second, since foam material 54B is acoustically transparent to the passband of interest (20 Hz to 1600 Hz), the sounds within the passband of interest pass through the foam material and into the resonant chamber formed by acoustic conduits 62 and 64 so that the sounds detected by microphone 54 have the desired tonal characteristics. Third, the energy dampening foam 54B keeps the microphone mechanically isolated (i.e., decoupled) from the flexible acoustic tube 14 so that any mechanical contact with flexible acoustic tube 14 does not introduce unwanted noise to the microphone.

A small diameter shielded cable 54A is used to connect the microphone 54 to the electronic circuitry in electronics housing 16. This shielded cable prevents any extraneous radio frequency noises from being picked up by the microphone circuit. Microphone cable 54A is preferably of a small enough diameter in order to remain flexible so that bending or flexing of the flexible acoustic tube 14 does not put strain on the microphone and/or the circuitry within electronics housing 16. As shown in FIG. 9C, shielded cable 54A is embedded within the material comprising flexible acoustic tube 14. Alternatively, shielded cable 54A could be routed through acoustic conduit 62, out through the open end 68 and then electrically connected to the circuitry in electronics housing 16.

Suspending microphone 54 in tube 14A allows the resonant frequency properties of the acoustic topology illustrated in FIGS. 9 and 9A to be preserved while reducing the extraneous noise that can be introduced to the microphone through the length of acoustic conduits 62 and 64 in the second acoustic topology illustrated in FIGS. 9 and 9A. Sounds introduced by the diaphragm in the chestpiece 12 can be detected by microphone 54 without distortion since large movements of the air in acoustic conduit 14A will travel past the microphone through foam 54B and will be vented through the open end 68 of acoustic conduit 62 rather than causing excessive pressure at the microphone.

Also, sounds introduced by the diaphragm of chestpiece 12 will be able to resonate in the chamber created by acoustic conduits 62 and 64 and these resonant sounds can be picked up by the microphone to create the natural and familiar sound produced by acoustic stethoscopes as in the second acoustic topology. Thus, low frequency, large intensity sounds from diaphragm 15 do not disrupt operation of the electronic stethoscope.

The third acoustic topology provides several additional advantages. First, by placing the microphone near the chestpiece, the microphone has greatly reduced sensitivity to noise introduced by the part of the flexible acoustic tube 14 between the microphone and the electronics housing. Consequently, extraneous noises are not picked up and amplified along with the desired heart and/or lung sounds. Similarly, extraneous noises produced by anything coming in contact with the flexible acoustic tube 14 (such as the user's fingers) do not create unwanted signals that reach the microphone and are subsequently amplified. This design has been found to reduce, to a greater extent than does the second acoustic topology, extraneous noise that could be picked up between the chestpiece and microphone transducer or noise that could be generated by contact with flexible acoustic tube 14.

In all other respects, including determination of the resonant frequency and varying the length of the acoustic conduits to vary the resonant frequency, the third acoustic topology operates in the same manner as the second acoustic topology. In one embodiment of the third acoustic topology, acoustic conduits 62 and 64 are both approximately twelve inches long and the acoustic path within the chestpiece 12 is approximately one inch. The resonant frequency of this total acoustic chamber formed by the chestpiece and the two acoustic conduits is approximately 136 Hz. The lengths of the acoustic conduits in this embodiment have been found to provide a "normal" and familiar sound to trained users of acoustic stethoscopes. The resonant frequency is within the range of typical acoustic stethoscopes designed for cardiac use.

The third acoustic topology may also include vents 26A, 30A in binaurals 28, 30, respectively. The vents serve to reduce excess air pressure in binarurals 28 and 30 generated by transducer 70 and/or by static pressure created when the earpieces are closed on the user's ears to thereby reduce any distortion that may reach the user's ears. Vents 26A and 30A can also be incorporated into the second acoustic topology illustrated in FIGS. 9 and 9A.

Figure 10:
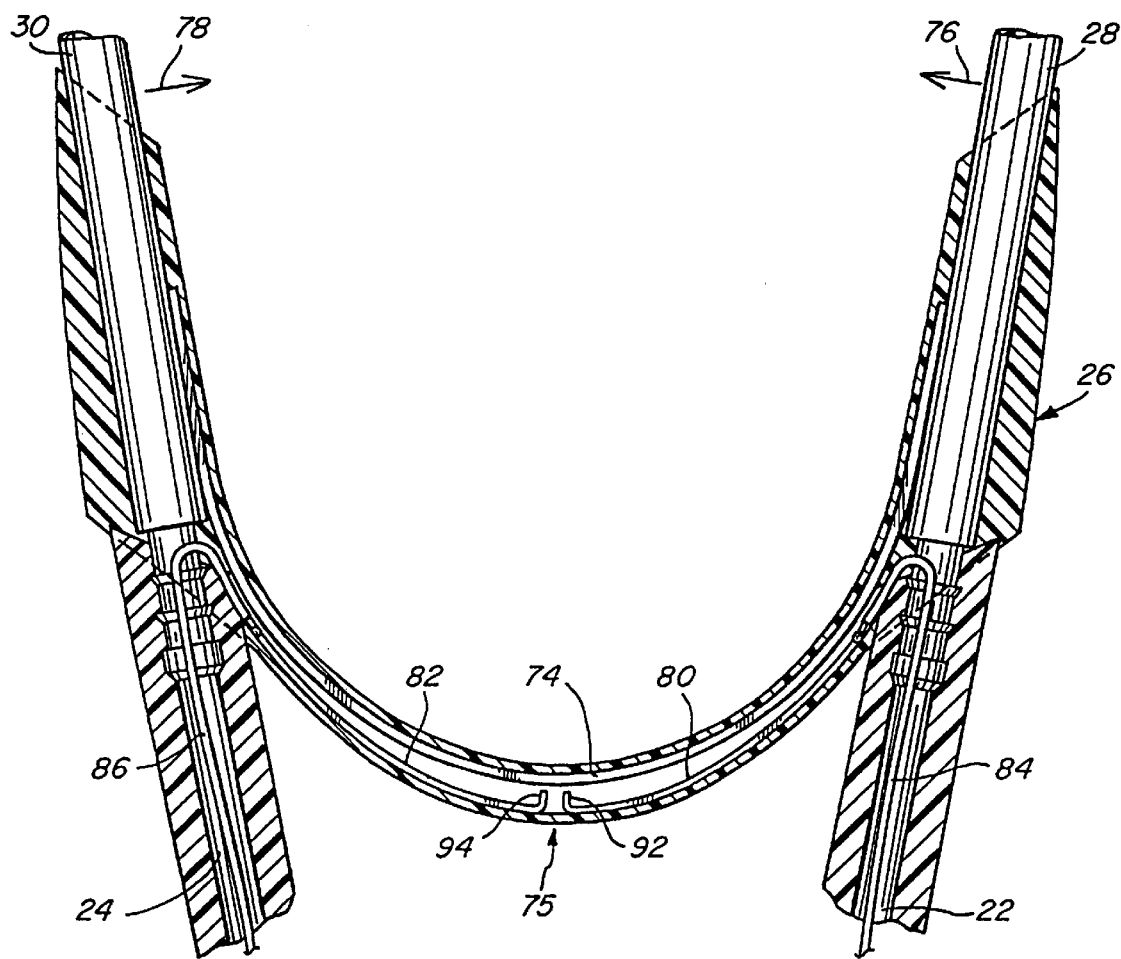
FIGS. 10 and 11 illustrate operation of the on/off switch used in the electronic stethoscope of FIG. 1.
Figure 11:
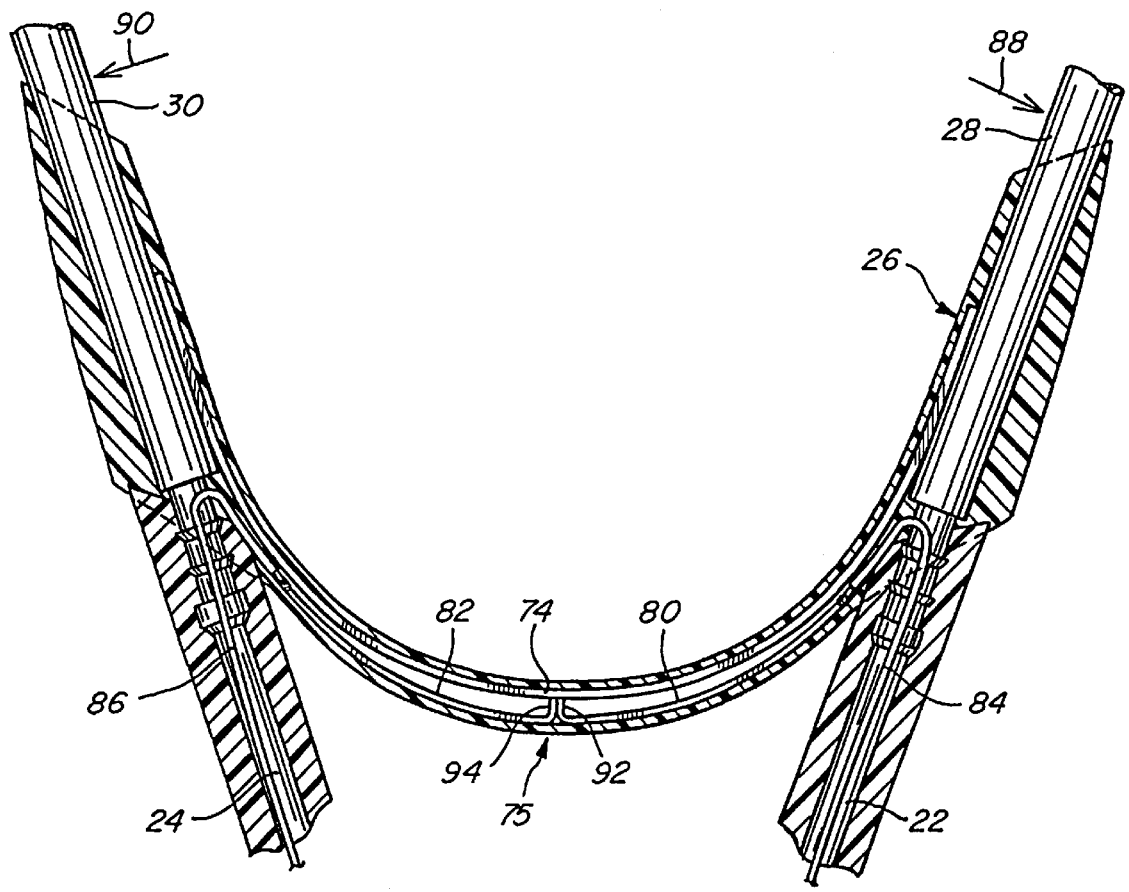

Another feature of the electronic stethoscope is the on/off switch 75 illustrated in FIGS. 10 and 11. As illustrated in FIGS. 10 and 11, spring and switch housing 26 contains a spring 74 having ends that are respectively attached to each binaural that applies closing pressure on the binaural so that binaurals 28 and 30 are continually urged towards each other in the direction of arrows 76 and 78. Two beryllium copper contacts 80 and 82 act as switch poles and are incorporated within spring and switch housing 26. A wire 84 is connected to contact 80 and runs from contact 80 outside binaural 28 and through the first acoustic conduit 22 to the circuitry contained within electronics housing 16. A wire 86 is connected to contact 82 and runs outside binaural 30 and through acoustic conduit 24 to the electronic circuitry contained within electronics housing 16. When the binaurals are pulled apart from their rest position along the direction of arrows 88 and 90 as shown in FIG. 11, in order to be placed in the user's ears, contact points 92 and 94 touch, turning on the electronic circuitry contained in electronics housing 16. When the user removes the stethoscope from his or her ears and spring 74 closes the binaurals together, contacts 92 and 94 are separated and the circuitry is shut off.

The symmetrical shape of the contacts allows simple fabrication. In addition, the right angle shape of contacts 92 and 94 allows precise control over the "turn on" point. Finally, the contact shape allows for a broad range of travel after the turn on point. Once contact points 92 and 94 of contacts 80 and 82, respectively, first touch, contacts 80 and 82 will simply bow as the binaurals are pushed further apart along the direction of arrows 88 and 90. Thus, continued separation of the binaurals along the direction of arrows 88 and 90 does not damage the on/off switch or interrupt the flow of power to the electronic circuitry.

This switch configuration provides a number of advantages. First, it eliminates the need for timer circuits (that automatically turn the electronic circuitry off after a predetermined time of nonuse) and manual on/off switches. Second, it eliminates the need for any standby currents that may drain the battery over time. Additionally, the switch and stethoscope are activated through normal usage and do not require any modification of the user's normal practice when using an acoustic stethoscope. Simply spread the binaurals and the stethoscope is turned on or allow the binaurals to close and the stethoscope is turned off.

In one embodiment of the invention, the switch 75 is activated when there is at least four inches of separation between the earpieces 36 and 38 of the binaurals. We have found that a four inch separation allows the electronic stethoscope to be turned on before being placed on a human head, while at the same time insuring that small (for example, accidental) separation of the binaurals will not turn on the stethoscope and inadvertently drain the battery.

An additional benefit of the spring switch assembly 75 is that it protects a user from being exposed to a transient signal resulting from the application of power to a highly amplified circuit. This transient could be harmful if earpieces 36 and 38 were already sealed to the user's ear canals. Since power is applied to the circuits by spring switch 75 before the earpieces reach the user's ears, any transient noise will have already passed and will not be heard by the user.

The spring 74 may be made of phosphor-bronze or spring steel which have the ability to maintain the original shape after bending. Unlike a conventional stethoscope, earpieces 36 and 38 do not need to be sealed as tightly to the user's ear canals because amplification is being provided. As a result, spring 74 can have a lower spring constant than springs of typical acoustic stethoscopes, thus making the electronic stethoscope of the invention more comfortable to use for extended periods of time. In one embodiment, spring 74 has a force of 0.5–0.6 pounds when the binaurals are separated by 4 to 5 inches.

Figure 11A:
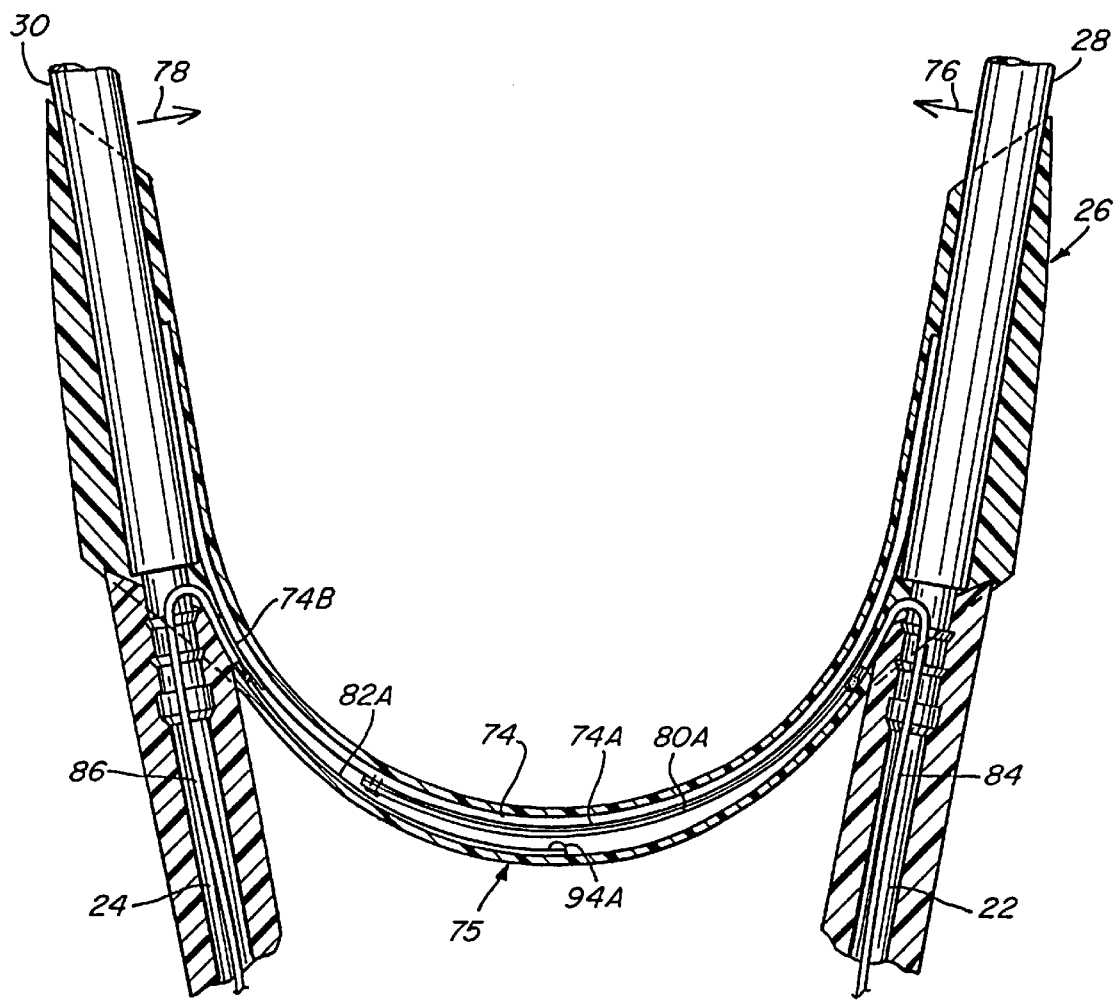
FIGS. 11A and 11B illustrate operation of an alternate embodiment of the on/off switch that may be used in the electronic stethoscope of FIG. 1.
Figure 11B:
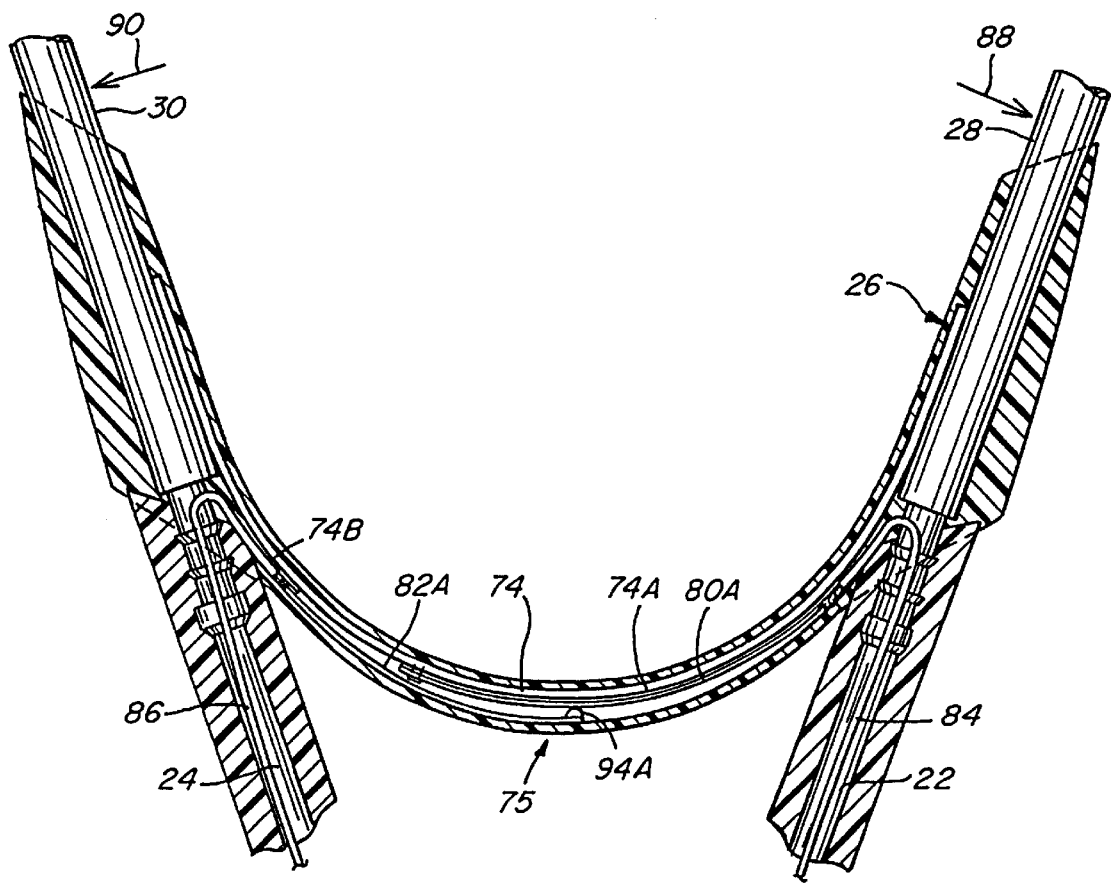

Reference is now made to FIGS. 11A and 11B which figures illustrate an alternate embodiment of the on/off switch 75. As illustrated in FIGS. 11A and 11B, the spring and switch housing 26 contains a spring 74 having ends that are respectively attached to each binaural that applies closing pressure on the binaural so that binaurals 28 and 30 are continually urged toward each other in a direction of arrows 76 and 78. An electrical insulator 74A is disposed between spring 74 and a first beryllium copper contact 80A. A second beryllium copper contact 82A is disposed inside housing 26 and spaced away from contact 80A. A separate insulator 74B may be disposed between contact 82A and spring 74. Alternatively, insulator 74A may extend along the entire length of spring 74. As with the embodiment of the spring switch illustrated in FIGS. 10 and 11, a wire 84 is connected to contact 80A and a wire 86 is connected to contact 82A. When the binaurals are pulled apart from their rest position along the direction of arrows 88 and 90 as shown in FIG. 11B, in order to be placed in the user's ears, contact 82A touches contact 80A, turning on the electronic circuitry contained in electronics housing 16. When the user removes the stethoscope from his or her ears and spring 74 closes the binaurals together, contacts 80A and 82A are separated and the circuitry is shut off.

The embodiment of the spring switch illustrated in FIGS. 11A and 11B also provides a precise turn on point as in the embodiment illustrated in FIGS. 10 and 11. Once contact 82A has made contact with contact 80A, contact point 94A travels along the length of contact 80A while maintaining an electrical connection even if the binaurals are separated far beyond their turn on point of approximately four inches separation. Consequently, the spring switch mechanism works consistently and reliably for many different head sizes. Preferably, spring 74 is made of spring steel because of its ability to maintain its original shape even after bending. In all other respects, the spring switch configuration illustrated in FIGS. 11A and 11B provides all of the same advantages as the switch configuration illustrated in FIGS. 10 and 11.

Figure 12:
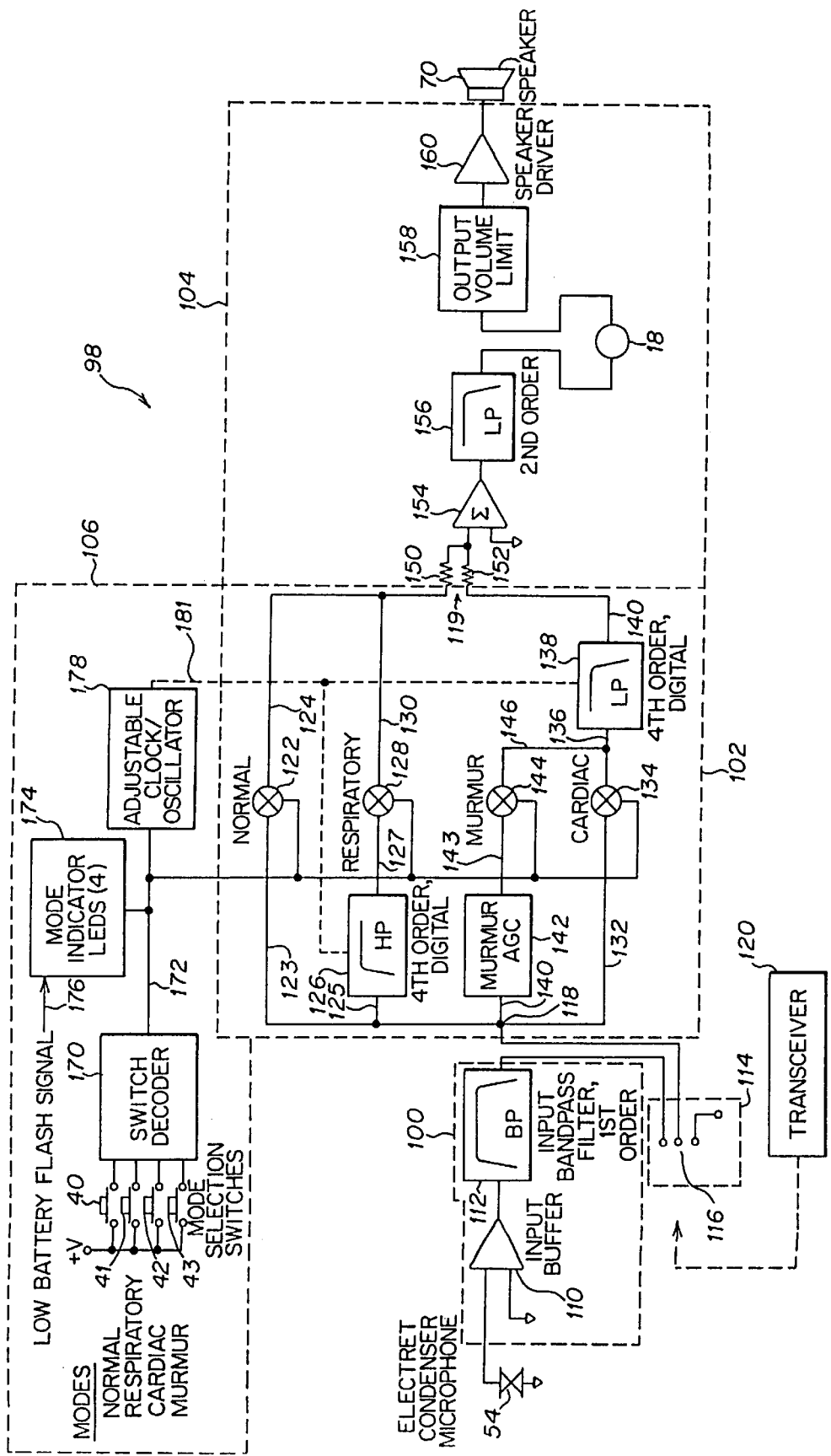
FIG. 12 is a schematic block diagram illustrating how the various processing functions of the electronic stethoscope of FIG. 1 are provided.

Reference is now made to FIG. 12 which is a block diagram of the circuitry contained within electronics housing 16 and which circuitry allows the electronic stethoscope of the invention to carry out a number of diagnostic functions.

The circuit 98 of FIG. 12 includes a number of sections. An input section 100 is used to condition electronic signals. A processing section 102 processes the electronic signals from the input section provided by microphone 54 according to the particular selected diagnostic function. An output section 104 receives the processed signals from processing section 102 and provides any necessary buffering and filtering of the signal before the output signal is sent to speaker 70. A control section 106 provides control signals for controlling the operation of processing section 102. Each of the sections will now be explained in detail.

Input section 100 receives an electronic signal from microphone 54 via buffer amplifier 110. From buffer amplifier 110, the signal is sent to an input bandpass filter 112. Bandpass filter 112 is an analog filter having a passband of between 20 and 1600 Hz. This pass band is the nominal pass band for heart and respiratory sounds. Signals having frequencies below 20 Hz are inaudible to the human ear and providing amplification for these sub-audio signals would consume excessive amplifier power and therefore, signals having a frequency below 20 Hz are filtered out. The output of the bandpass filter 112 is wired to a transceiver interface 114. Transceiver interface 114 includes a normally closed switch 116 that under normal conditions, passes the signal from bandpass filter 112 to the input 118 of processing section 102. Transceiver interface 114 provides an interface allowing the electronic stethoscope to send signals to another device, such as a second electronic stethoscope, or allows the electronic stethoscope to receive signals from another device, such as a second electronic stethoscope to allow more than one user to hear and participate in the diagnosis of the same biological activity. The connection between electronic stethoscopes can be a wired or wireless connection. When a transceiver is plugged into transceiver interface 114 and the transceiver is receiving a signal, the signal from chestpiece 12 is disconnected from processing section 102 to prevent interference. When a transceiver is plugged into transceiver interface 114 and the transceiver is transmitting a signal, circuitry in the transceiver also routes the signal from chestpiece 12 to processing section 102. Transceiver interface 114 also allows a signal that is detected by chestpiece 12 to be recorded for later diagnosis. In the same way, a prerecorded signal can be fed into processing section 102 for diagnosis by a user.

A transceiver, such as transceiver 120 may also be used to transmit the signals detected by the electronic stethoscope to a remote destination or to receive signals from a remote source. Transceiver 120 may be an infrared or radio-frequency transceiver. The transceiver may be capable of transmitting only, receiving only, or transmitting and receiving signals. An infrared transceiver is preferred because infrared signals do not cause interference to other radio-frequency devices and are not subject to radio-frequency interference from other devices. Interference is of particular concern in environments such as hospitals where many radio-frequency devices are used. Since infrared transmission is "line-of-sight", it does not interfere with devices, for example, in other rooms. The use of a transceiver, such as transceiver 120, allows the electronic stethoscope to transmit and receive electronic signals using a wireless connection.

The signal from either input bandpass filter 112 or transceiver 120 is sent to the input 118 of processing section 102. Processing section 102, under control of control section 106, processes the electronic signals received at input 118 and provides these signals to output 119.

Processing section 102 has four modes of operation. Each mode will be explained separately.

When the "normal" mode is selected, the acoustic output of the electronic stethoscope emulates the output of a typical acoustic stethoscope. In the normal mode, the processing circuitry provides substantially flat frequency response between 20 and 1600 Hz while filtering out sounds outside of the pass band. In the normal mode of operation, the signal from input 118 passes only through selector 122 (from line 123) before being transmitted to output section 104 on line 124. Input bandpass filter 112 removes harmonic resonances created by the acoustic tubing of the stethoscope, which tubing can pick up unwanted sounds outside of the desired pass band. As a result, the user hears substantially only the sounds generated by the heart and lungs having spectral characteristics determined by the acoustic topology of the stethoscope.

When the "respiratory" mode is selected, the electronic stethoscope provides acoustic signals generated substantially only by the lungs. In the respiratory mode, the signal from input 118 is sent along line 125 to a fourth order high-pass Butterworth digital filter 126 having a corner frequency at approximately 140 Hz. The nominal pass band for normal and abnormal human breathing sounds is approximately 140 to 1600 Hz. We have determined that the corner frequency of high pass filter 126 should be in the range of 100 to 300 Hz. We have found that a corner frequency of approximately 140 Hz provides a workable tradeoff between the need to avoid extraneous signals and the need to include signals having significant diagnostic information. The output of high pass filter 126 is routed along line 127 through selector 128 along line 130 to output section 104. In the respiratory mode, the user hears substantially only the acoustic sounds generated by the biological activity of the lungs.

When the "cardiac" mode is selected, the acoustic output of the electronic stethoscope contains substantially only acoustic signals generated by biological activity of the heart. In the cardiac mode, the signal passes from input 118 along line 132 through selector 134 and line 136 to a fourth order, low pass, Butterworth digital filter 138. The output of filter 138 is sent along line 140 to processing section 104. Low pass filter 138 is set with a corner frequency of approximately 480 Hz. The nominal pass band for normal and abnormal heart sounds is between approximately 20 and 600 Hz. We have determined that the corner frequency of low pass filter 138 should be in the range of 400 to 600 Hz. We have found that a corner frequency of approximately 480 Hz provides a workable tradeoff between the need to avoid extraneous signals and the need to include signals having significant diagnostic information. As a result of filtering by low pass filter 138, in the cardiac mode, the user hears substantially only the sounds generated by biological activity of the heart.

When the "murmur enhancement" mode is selected, the electronic stethoscope disproportionally amplifies acoustic signals generated by normal and abnormal cardiac activity. In the murmur enhancement mode, the electronic signal at input 118 is sent along line 140 to an automatic gain control circuit 142. From automatic gain control circuit 142, the signal passes through selector 144 along line 146 to low pass filter 138. In the murmur enhancement mode, both the murmur automatic gain control circuit 142 and low pass filter 138 are used so that the user hears substantially only enhanced abnormal heart sounds (i.e., heart murmurs) and normal (i.e., so called dominant or first and second) heart sounds. This mode provides disproportionate amplification of heart murmurs relative to dominant heart sounds so as to enhance heart murmur diagnosis.

Heart murmurs are sounds generated by abnormalities in the heart. Typically, heart murmurs are very low in intensity relative to the first and second heart sounds. Heart murmurs often can occur within a few milliseconds of the beginning or end of the first or second heart sound. In the murmur enhancement mode, the output signal on line 140 includes a signal of the first and second heart sounds having slight amplification with low level heart sounds, such as murmurs, being amplified to a level that makes them clearly audible compared to the dominant heart sounds. In the murmur enhancement mode, the timing between and among and the frequency characteristics of the first, second, and abnormal heart sounds is preserved from input 118 to the output of low pass filter 138 (and throughout the entire signal path of the electronic stethoscope). This is especially advantageous because the timing of the heart murmur relative to the first and second heart sounds can be an important factor in diagnosing the heart abnormality. In addition, preserving the frequency characteristics of the normal and abnormal heart sounds provides familiar sounds that a user is trained and accustomed to hear.

To accomplish this result, the time constant of the automatic gain control circuit 142 has a relatively short duration. The time constant should be set so that it is long enough to avoid introducing any noticeable distortion into the sounds heard by the user. In addition, the time constant should be short enough so that the automatic gain control circuit can respond to a rapid change in the volume level on line 140 resulting from the transition between dominant heart sounds and murmurs. We have found that a time constant having a range of 5 to 10 milliseconds and centered around 10 milliseconds provides a workable balance between the requirements for the time constant. A time constant of 10 milliseconds allows automatic gain control 142 to track normal and murmur heart sounds to provide amplification for each signal so that the output of the automatic gain control circuit 142 on line 146 contains slightly amplified normal heart sounds and clearly audible murmur sounds. The short time constant allows automatic gain control circuit 142 to increase the output level of a low level murmur that occurs immediately after a relatively loud dominant heart sound by responding rapidly to the decay in the normal heart sound signal. Similarly, the relatively short time constant allows the automatic gain control circuit to rapidly respond to the increased volume level of a dominant heart sound which follows a low level murmur and to reduce the gain accordingly so that the relatively loud normal heart sound is not amplified significantly and any resulting distortion is substantially inaudible.

Since murmur sounds may have an extremely low intensity level and automatic gain control circuit 142 can provide only a fixed maximum gain, not all murmurs can be amplified to a level that is substantially the same as the dominant heart sounds. Therefore, automatic gain control circuit 142 provides the low level murmur sounds with maximum gain so as to reduce the difference in intensity level between the murmur sounds and the dominant heart sounds. This is what is meant by disproportionate amplification.

Figure 12A:
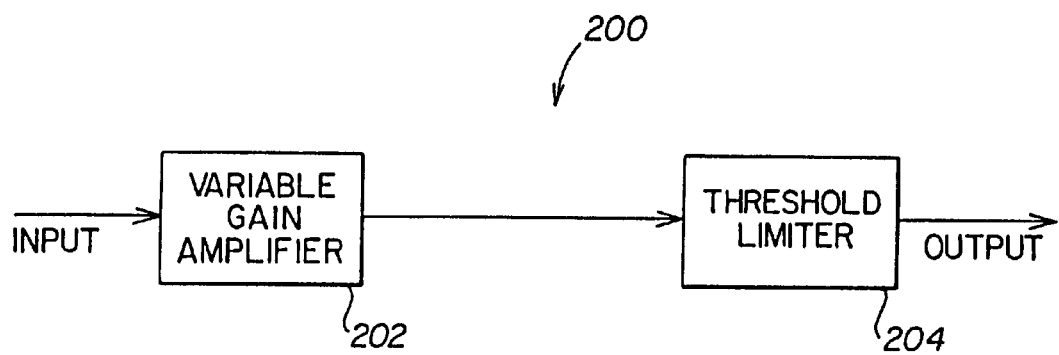
FIGS. 12A and 12B illustrate alternative embodiments for providing the murmur enhancement processing function.
Figure 12B:
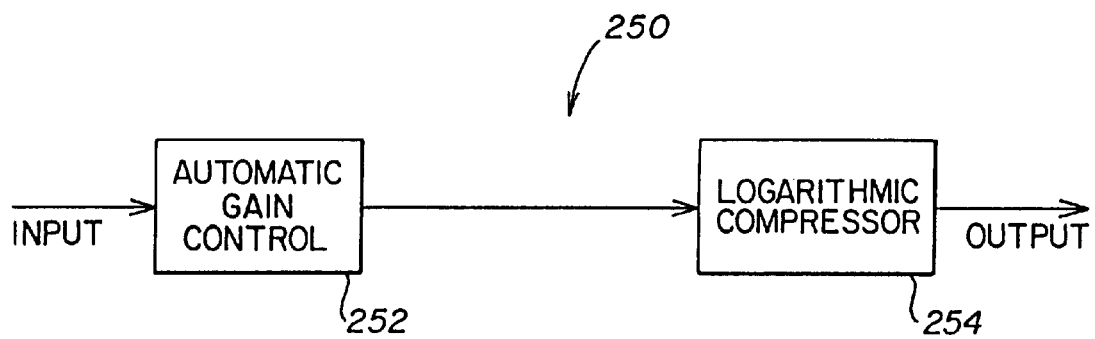

Reference is now made to FIGS. 12A and 12B which figures illustrate alternative circuits for providing the murmur enhancement function. Circuit 200 illustrated in FIG. 12A uses a variable gain amplifier 202 followed by a threshold limiter 204. Variable gain amplifier 202 amplifies all of the signals from bandpass filter 112. The amplified signals are then sent to threshold limiter 204 having a preset threshold. When the dominant heart sounds reach the threshold of the limiter, they are prohibited from being further amplified. Meanwhile, the gain of the variable gain amplifier 202 is set to increase the level of the lower level murmur sounds while the output volume of the dominant heart sounds is held constant. Although this circuit performs the desired murmur enhancement function, when the dominant heart sounds reach the threshold of the threshold limiter and the gain of variable gain amplifier 202 is increased, limiting of the dominant heart sounds may cause audible distortion.

Circuit 250 illustrated in FIG. 12B uses an analog automatic gain control circuit 252 followed by a logarithmic compressor 254. Automatic gain control circuit 252 provides a constant average output volume level that is independent of the level of the input signal. To achieve the desired transfer response, the nominal volume level, the time constant, and the maximum gain provided in the presence of a low level or no input signal are set. As a result, automatic gain control circuit 252 normalizes the input signal so that the signal provided to logarithmic compressor 254 is at a substantially constant level. The time constant of the automatic gain control circuit is set to a duration of several seconds so that it covers several heartbeats. The output of automatic gain control circuit 252 is therefore a scaled version of the input signal. Logarithmic compressor 254 operates in a logarithmic manner to compress the signal provided by automatic gain control circuit 254 in order to accentuate the low level signals.

Although the circuit in FIG. 12B operates to perform the desired murmur enhancement function, it also suffers from the same limitations of circuit 200 in FIG. 12A. In addition, since a relatively long time constant is used to normalize the signal level delivered by the automatic gain control circuit, it is possible for the user to hear the automatic gain control circuit working. For example, the user may first hear the level of the heart sounds at one level while the automatic gain control circuit time constant sets the normalized output level. Once the normalized output level is set, the volume heard by the user may change.

One skilled in the art will appreciate that the variable gain amplifier 202 and the logarithmic compressor 254 could also be used in combination to perform the murmur enhancement function. One skilled in the art will also appreciate that the automatic gain control 252 and the threshold limiter 204 could also be used in combination to perform the murmur enhancement function.

Although the operation of the murmur enhancement circuit has been explained for the case in which the abnormal heart sounds are at a lower level than the normal heart sounds, there are occasions when the abnormal heart sounds are actually louder than the normal heart sounds. In this situation, the murmur enhancement circuit operates to amplify the normal heart sounds and provide relatively little amplification for the abnormal sounds. Thus, the circuit can provide amplification for the abnormal heart sound or the normal heart sound, depending upon which sound is of lower intensity.

One skilled in the art will appreciate that although filter 138 is connected to the output of automatic gain control circuit 142 in the illustrated embodiment, these devices could be connected so that the signal is filtered first by filter 138 and then gain controlled by automatic gain control circuit 142. In the same manner, the circuits of FIGS. 12A and 12B can be placed before or after filter 138.

When in the murmur enhancement mode, the corner frequency of low pass filter 138 may be the same as the corner frequency when the stethoscope is operating in the cardiac mode. Alternatively, the corner frequency for low pass filter 138 when the stethoscope is operating in the murmur enhancement mode can be different from the corner frequency used in the cardiac mode. The corner frequency for low pass filter 138 can be set at any frequency between the cardiac corner frequency and the overall bandwidth for the electronic stethoscope (approximately 1600 Hz in one embodiment). For example, if, in the murmur enhancement mode, the corner frequency of low pass filter 138 is set to 1600 Hz, high frequency sounds such as those made by prosthetic heart values can be monitored. As explained hereinafter, adjustable clock/oscillator circuit 178 is used to provide a control signal that changes the corner frequency of low pass filter 138. As a result, the corner frequencies of the filters (for example, filter 126 and filter 138) in processing section 104 can be set independently for each mode of operation of the electronic stethoscope.

The output at 119 of processing section 102 is provided to resistors 150 and 152 which are coupled to the input of a summer 154. The output of summer 154 is passed through a second order low pass filter having a corner frequency at approximately 1600 Hz to further limit any extraneous noise from being passed through the circuit to the user. From filter 156, the signal is passed to the gain control (having a gain set by control knob 18) and to an output volume limiter 158 that includes a limiter having an adjustable threshold that can be pre-set. The threshold is set so that sounds introduced into the chestpiece, from, for example, loud voices, banging of the chestpiece on a hard surface or loud ambient noises, cannot exceed a certain level that could potentially damage the user's ears. From the output volume limiter, the signal is amplified by a speaker driver amplifier 160 and then provided to speaker 70.

Processing section 102 is controlled by control section 106. Control section 106 includes a number of mode switches, 40–43 coupled to a switch decoder 170. Each of the modes of operation of the electronic stethoscope is selected by momentarily depressing the corresponding mode switch. Switch decoder 170 responds to the activation of mode switches 40–43 to respectively activate selectors 122, 128, 144, and 134 to provide the desired mode of operation via control line 172. The control signal from switch decoder 170 on control line 172 is also provided to a mode indicator control circuit 174 that supplies power to indicators 20, 21, 23, and 25, respectively, depending on which mode has been selected. A single indicator is illuminated for each mode of operation. A low battery flash signal 176 is also provided to indicator control circuit 174 causing mode indicator control circuit 174 to flash the currently illuminated indicator when the battery voltage drops below a predetermined level. This signal may also be used to control output section 104 to provide an audio signal when the battery voltage drops below the predetermined level. We have chosen a threshold of 1.0 volts because the stethoscope is able to continue operating for several hours when the supply voltage reaches this level. This provides a warning to the user that, although the supply voltage is low, there is sufficient power available for a few more hours of operation. This type of warning is advantageous because the user is warned before the stethoscope actually stops operating which is important in, for example, emergency situations. It also provides a familiar mode of operation, since acoustic stethoscopes do not simply stop functioning, thus making the operation of the electronic stethoscope similar to an acoustic stethoscope.

In one mode of operation, the electronic stethoscope defaults to the normal mode of operation whenever the stethoscope is turned on. Alternatively, if switch decoder 170 is powered directly by the battery that powers the electronic circuitry, then the electronic stethoscope can maintain the last mode that was selected before the stethoscope was turned off by closing of the binaurals. When the power is turned off, a very small current from the battery to switch decoder 170 will keep the last mode selected by switch decoder 170 active. Therefore, when the stethoscope is turned on the next time, switch decoder 170 will default to the last mode selected rather than to the normal mode.

Signal 172 is also provided to an adjustable clock/oscillator circuit 178. Circuit 178 provides control signals on line 180 to control the corner frequencies of the digital filters used in processing section 102, such as filters 126 and 138. The use of digital filters in processing section 102 allows the corner frequencies of the filters to be adjusted depending upon the particular application. For example, the described corner frequencies are typically used to detect heart and lung sounds in adults and adolescents. However, we have determined that the frequencies of the acoustic signals of heart and lung sounds of infants and children are higher than those of adults or adolescents. As a result, the corner frequencies of the filters need to be increased. This increase in a corner frequency can be accomplished electronically by changing the frequency of the clock signal provided by clock/oscillator 178 on line 180. A switch (for example 179 in the circuit of FIGS. 13A, 13B) in clock/oscillator circuit 178 may be activated to provide a new set of corner frequencies on control line 180 that are appropriate for detecting heart and lung sounds of infants and children. In all other respects, the operation of the circuit is as previously described.

This capability of modifying the corner frequencies of the filters is especially advantageous. Conventionally, if the heart and lung sounds in infants and children are desired to be detected, a pediatric acoustic stethoscope, generally having a smaller chestpiece and acoustic tubing designed to accentuate the higher frequencies is used. Alternatively, an adult acoustic stethoscope may have an adapter attached to the chestpiece designed to be more responsive to the higher frequencies. The present invention eliminates the need for modification of a stethoscope or the need for a separate stethoscope for infants and children. One skilled in the art will appreciate that circuit 178 can be controlled so as to produce a control frequency on line 180 that may be higher or lower than the discussed corner frequencies and that these control frequencies can be selected to be appropriate for the particular type of diagnosis being performed.

The use of filters having gains which can be set in processing section 102 is also advantageous because it allows the signals provided at node 119 to be normalized to the signal level in the normal mode on line 124 for all modes of operation. By controlling the respective gains of filters 126 and 128 the level of the electronic signal on lines 130 and 140 can be adjusted so that it is substantially the same as the signal level of the electronic signal on line 124. Since the signal level on lines 130 and 140 is substantially the same as the signal level on line 124, the output of processing section 102 (and the electronic stethoscope as a result) is substantially the same level without regard to the particular mode of operation chosen. This provides several advantages. First, a user does not have to increase the volume manually when switching from a mode with high amplification (for example, the murmur enhancement mode) to a mode with relatively low amplification (for example, the normal mode). In addition, the user is protected from excessive transients and amplification when switching from a mode having relatively low amplification (for example, the normal mode) to a mode of operation have a relatively high amplification (for example, the murmur enhancement mode).

One skilled in the art will appreciate that although filters 112 and 156 are analog filters in the illustrated embodiment, these filters could be implemented using digital technology. One skilled in the art will also appreciate that although filters 126 and 138 are digital filters in the illustrated embodiment, these filters could be implemented using analog technology.

Figure 12C:
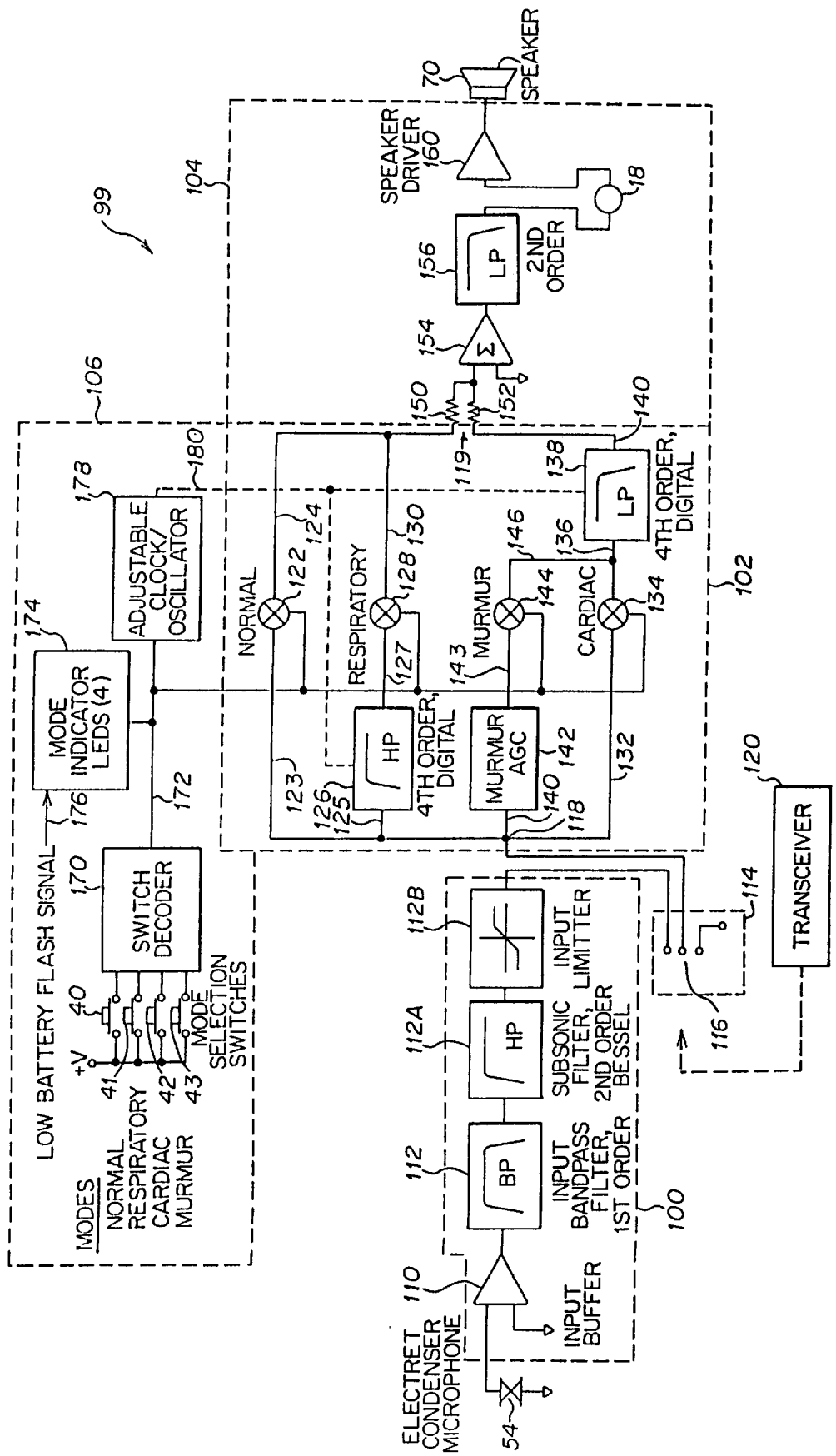
FIG. 12C is an alternate schematic block diagram illustrating how the various processing functions of the electronic stethoscope of FIG. 1 are provided.

Reference is now made to FIG. 12C, which figure illustrates an alternate embodiment of the circuitry contained within electronics housing 16 and which allows the electronic stethoscope of the invention to carry out the previously discussed diagnostic functions. In the circuit of FIG. 12C, output volume limiter 158 has been eliminated. In addition, a subsonic filter 112A and input limiter 112B process the signal coming from band pass filter 112 before it is sent to processing section 102. In all other respects, the operation of the circuit of FIG. 12C is the same as described in connection with FIG. 12.

The subsonic filter 112A helps to more sharply filter out subsonic signals (i.e., signals below approximately 20 Hz which are inaudible to the human ear) that cause distortion and/or consume excess amplifier power. The corner frequency of subsonic filter 112A is set at approximately 35 Hz. As discussed previously, in order that the electronic stethoscope of the invention have the same acoustic characteristics as a normal acoustic stethoscope, signals below approximately 20 Hz should be attenuated as much as possible. Experiments indicate that increasing the corner frequency to much more than 35 Hz produces a noticeable, audible low frequency rolloff which could decrease the ability of the electronic stethoscope to reproduce very low frequency sounds that are still audible. Decreasing the corner frequency below 30 Hz produces no appreciable attenuation of signals below 20 Hz unless a higher order filter is used. In one embodiment of the invention, subsonic filter 112A is a second order Bessel high pass filter with a corner frequency of 35 Hz. Experiments indicate that the second order Bessel high pass filter using a corner frequency of 35 Hz produces a reasonable tradeoff between the desired attenuation and the complications associated with the use of higher order filters that could be used to obtain a sharper frequency rolloff with a lower corner frequency.

The output of subsonic filter 112A is supplied to input limiter 112B. Input limiter 112B reduces the impact sounds of the user's fingers touching the chestpiece and/or flexible acoustic tube 14. Input limiter 112B limits the magnitude of the input signals supplied to processing section 102 in a predictable manner so that large sudden transients do not cause noise and/or distortion in the user's ears. The threshold level set for the limiter does not affect normal and abnormal heart and/or lung sounds and these signals pass through the filter stages unchanged. However, sharp, high intensity impact noises caused by, for example, the user's fingers moving against the surface of the chestpiece or flexible acoustic tube 14 are substantially reduced by input limiter 112B. In one embodiment of the invention, input limiter 112B may use an operational amplifier with a virtual ground set at 2.5 volts and the limiter threshold set at 1.5 volts above and below the virtual ground level. The limiter is an active circuit, including a diode and operational amplifier clamping circuit that provides hard limiting at the 1.5 volt threshold. The gains of input buffer 110, input band pass filter 112, and subsonic filter 112A are set to bring the maximum normal signal level to approximately 1.5 volts and the stages following the limiter, i.e. processing section 102 and output section 104, are set to be responsive to this predictable 1.5 volt limit. Signals that are in excess of the normal 1.5 volt level are clamped by the limiter circuit at the 1.5 volt level threshold. One advantage of this particular circuit configuration is that the input limiter provides a fixed limit threshold regardless of the volume level set in output section 104.

Figures 1, 13A:
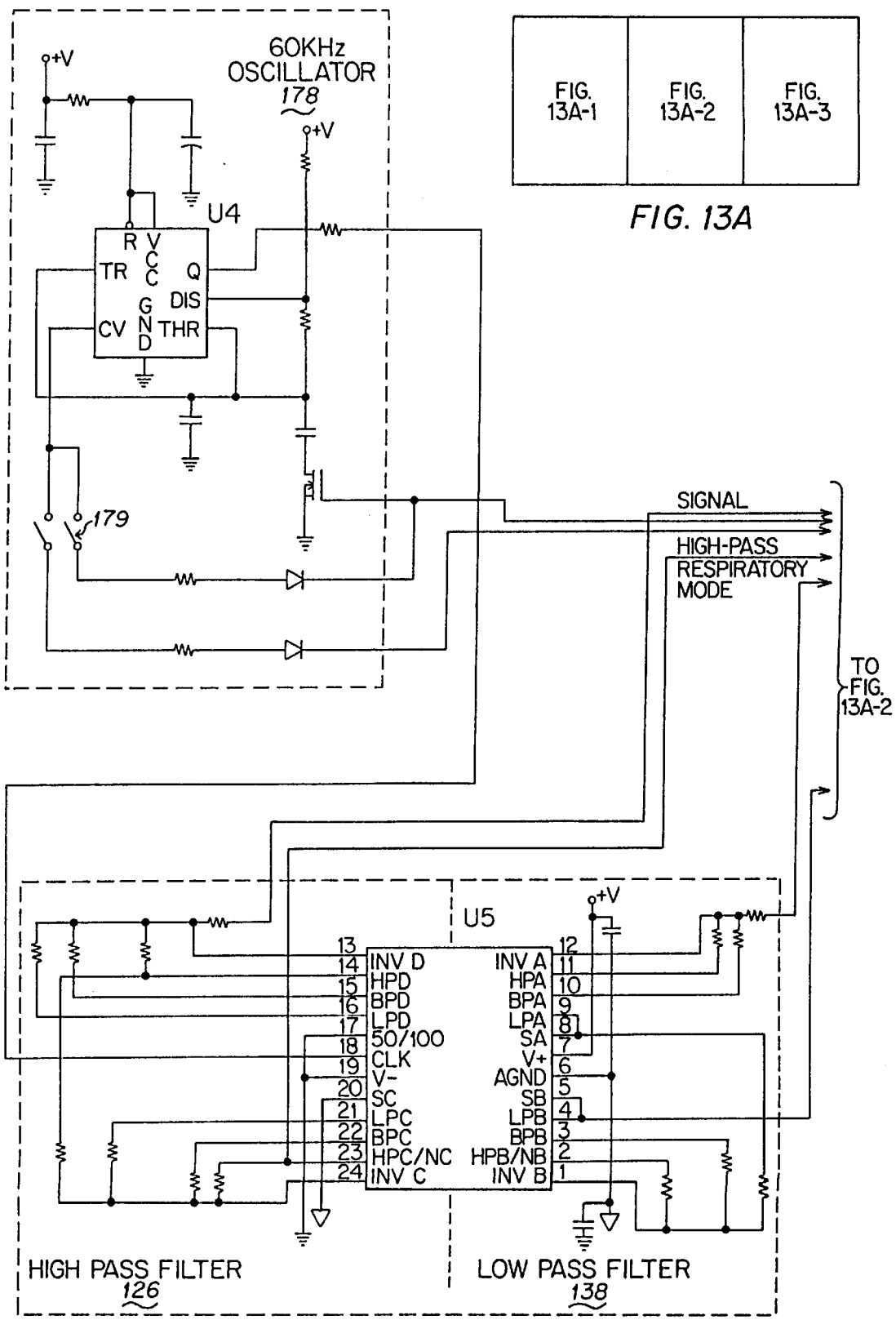
FIGS. 13A and 13B illustrate an exemplary circuit implementation of the block diagram illustrated in FIG. 12.
Figures 2, 13A:
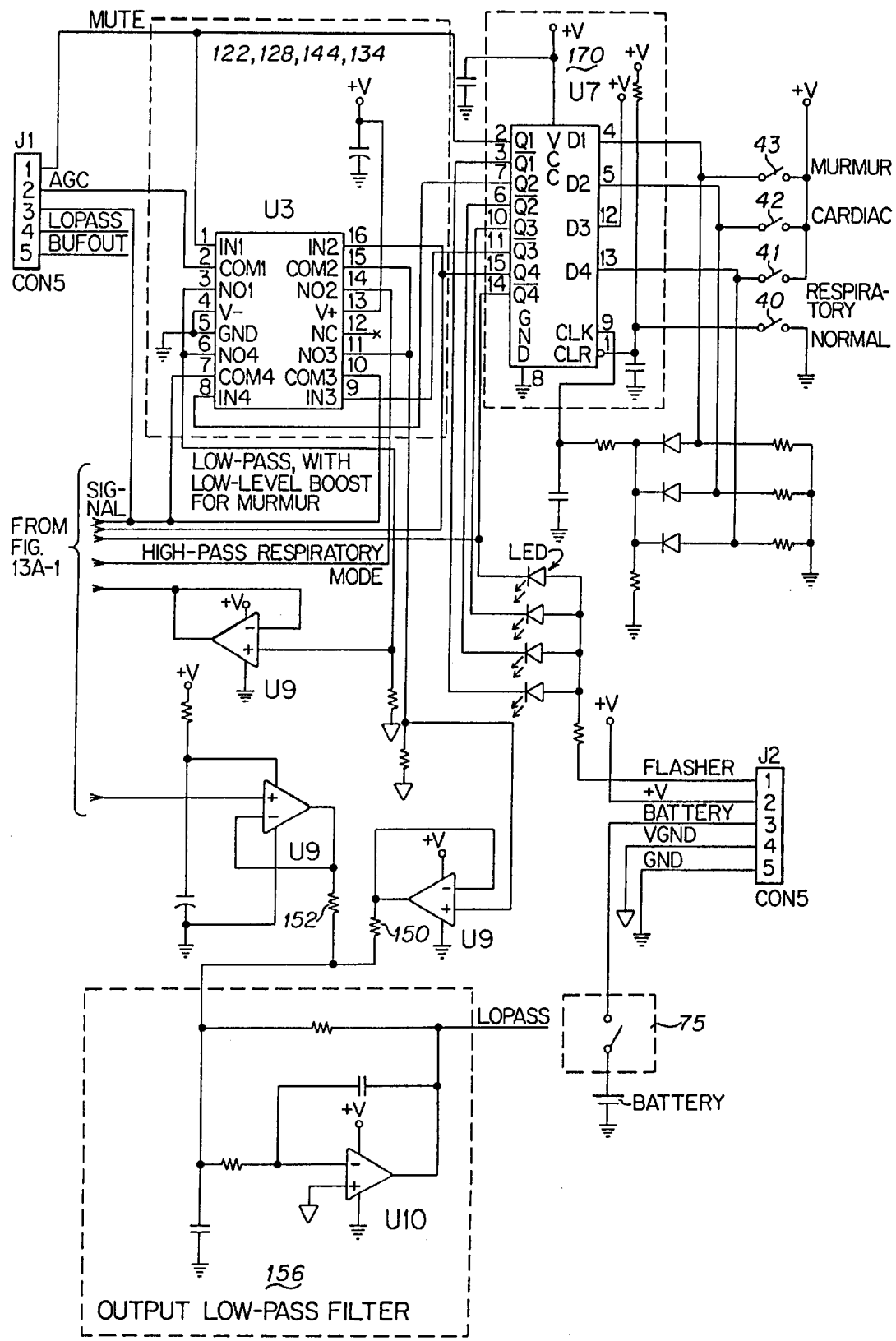
Figures 3, 13A:
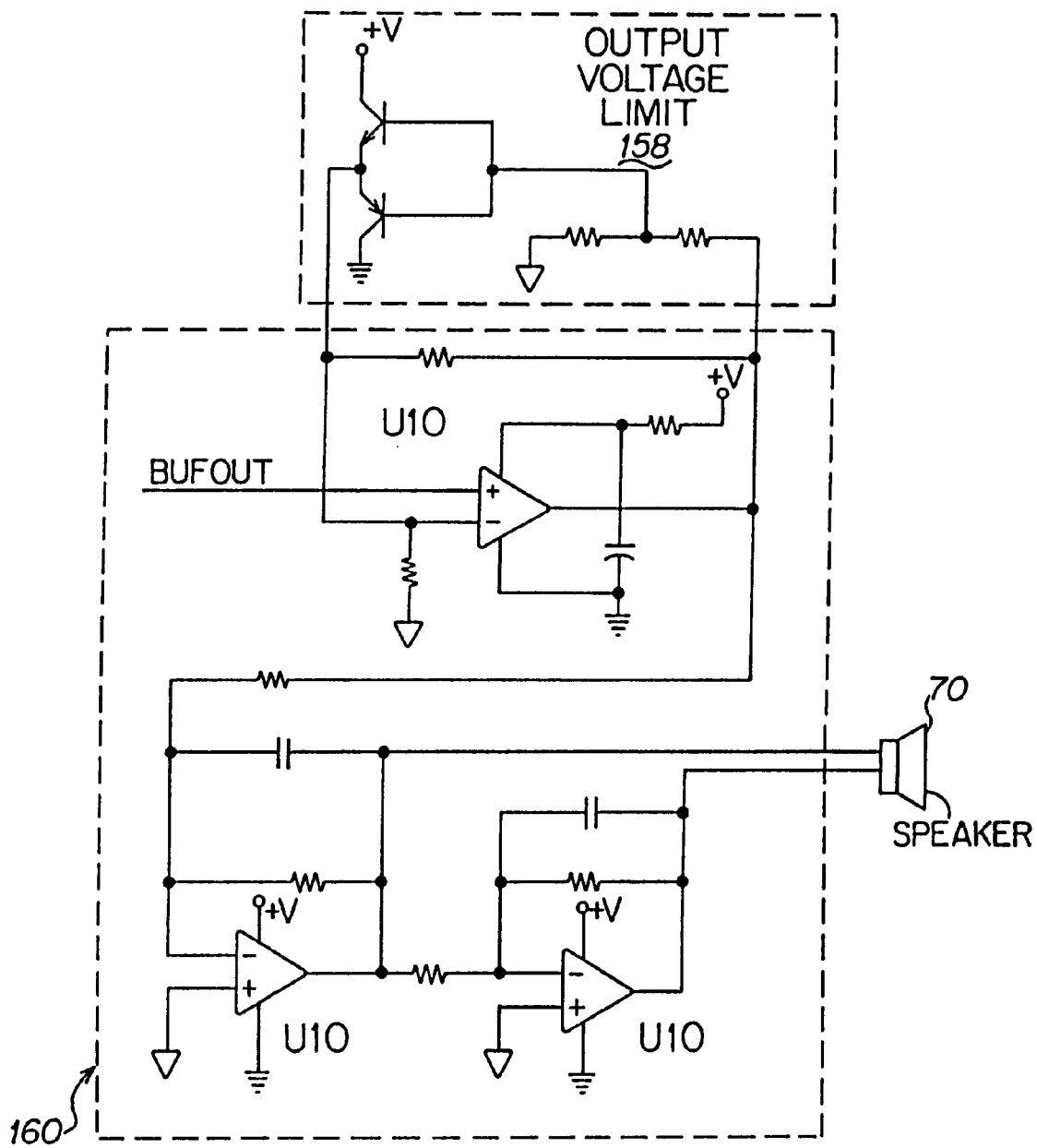
Figures 1, 13B:
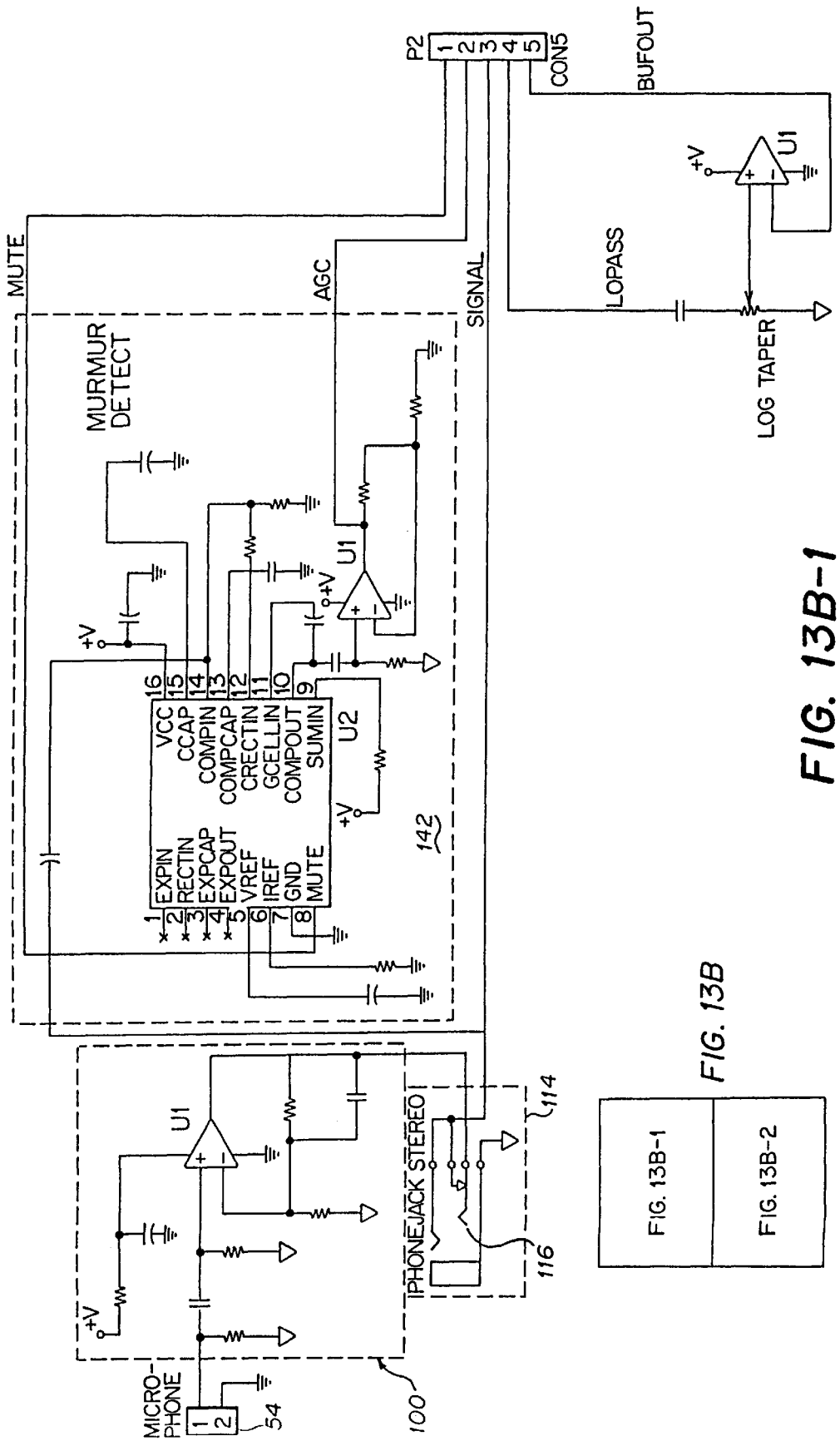
Figures 2, 13B:
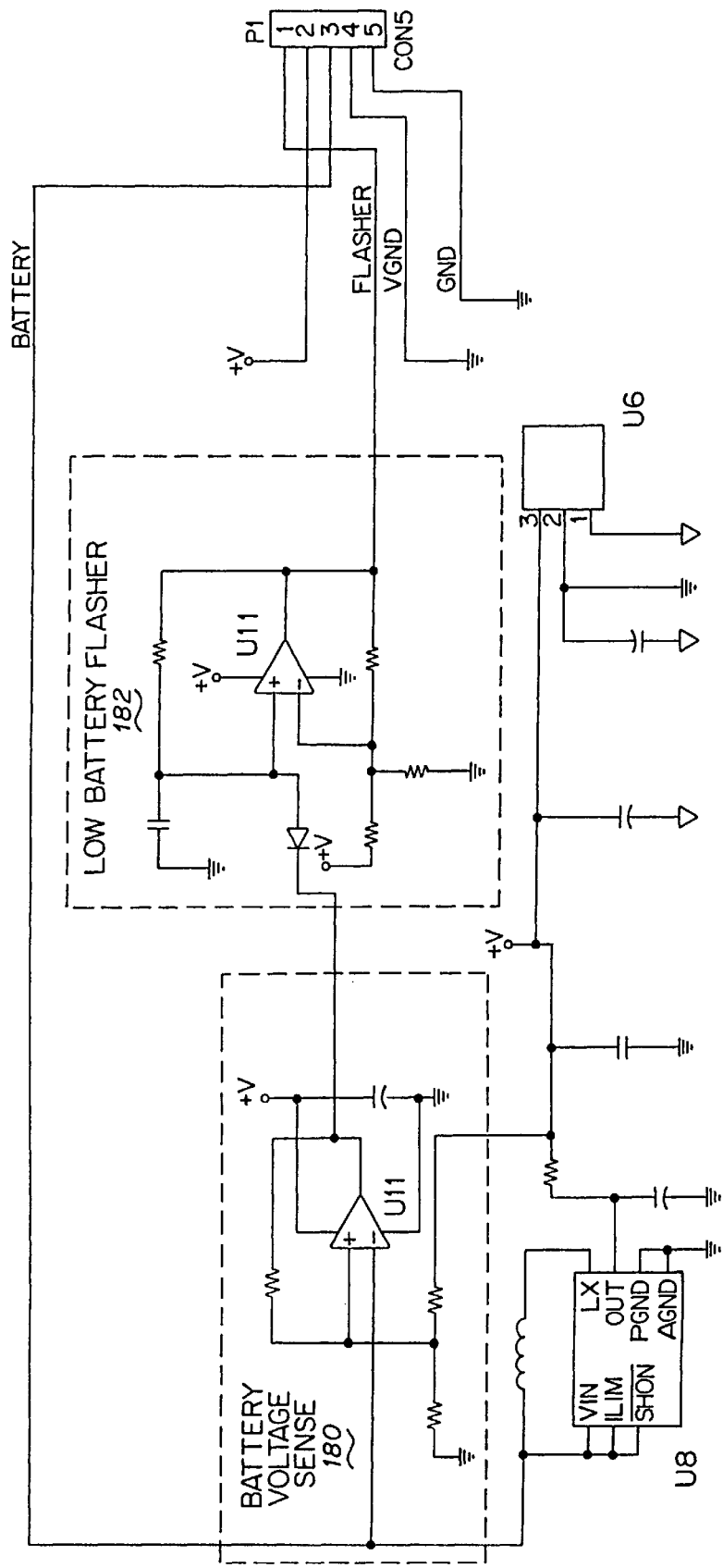

Reference is now made to FIGS. 13A and 13B, which Figures are a schematic diagram of an illustrative circuit embodiment of the block diagram of FIG. 12. The illustrated circuit can be powered by a single "AA" alkaline battery and can provide approximately 30 hours of operation. If a lithium "AA" battery is used, the circuit can operate for approximately 90 hours. A battery voltage sensing circuit 180 monitors the battery voltage level and controls low battery flasher circuit 182 to flash the then-illuminated indicator to warn that the battery needs replacement. The integrated circuits used in the circuit of FIGS. 13A and 13B are listed below:

| Integrated Circuit List (FIGS. 13A and 13B) | | | |
|---|---|---|---|
| IC# | Part # | Manufacturer | Description |
| U1 | LMC662C | National Semiconductor | dual op amp |
| U2 | NE578 | Philips/Signetics | compressor/expander (AGC function) |
| U3 | MAX392 | Maxim | quad switch |
| U4 | LMC555C | National Semiconductor | timer |
| U5 | LTC1164 | Linear Technology | switched capacitor programmable filter |
| U6 | TLE2425C | Texas Instruments | virtual ground generator |
| U7 | 74HC175 | Motorola | quad D flip flop |
| U8 | MAX777 | Maxim | dc to dc converter controller 1 battery cell step-up |
| U9 | LMC660C | National Semiconductor | quad op amp |
| U10 | LMC660C | National Semiconductor | quad op amp |
| U11 | LMC662C | National Semiconductor | dual op amp |

Figures 2, 14A:
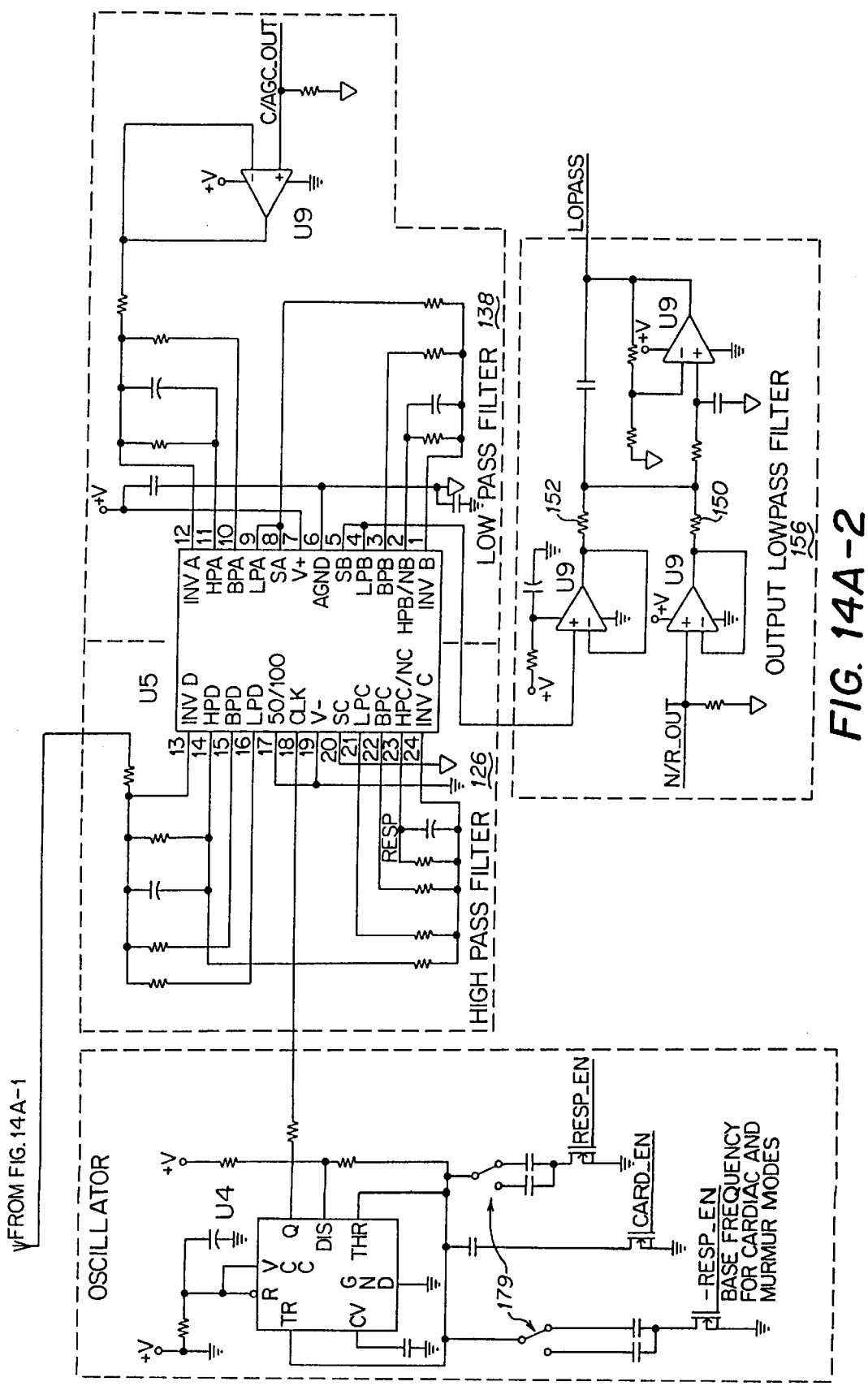
FIGS. 14A and 14B illustrate an exemplary circuit implementation of the block diagram illustrated in FIG. 12C.
Figures 3, 14A:
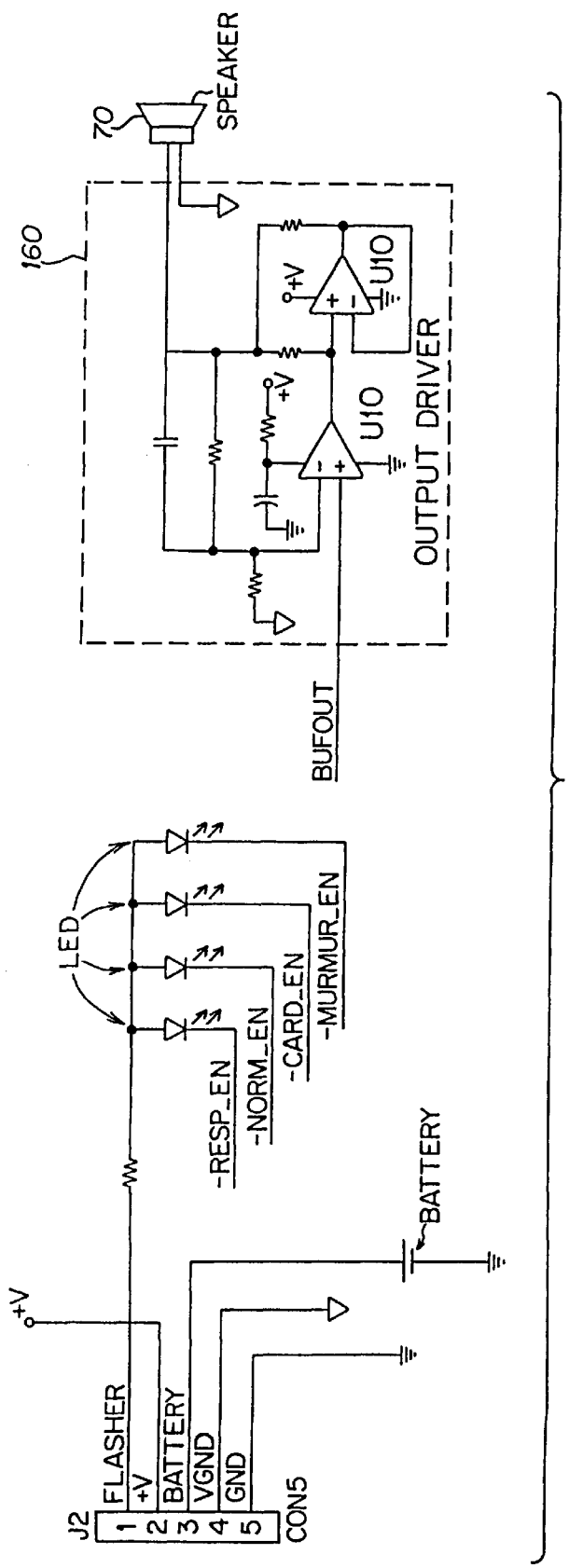
Figures 1, 14B:
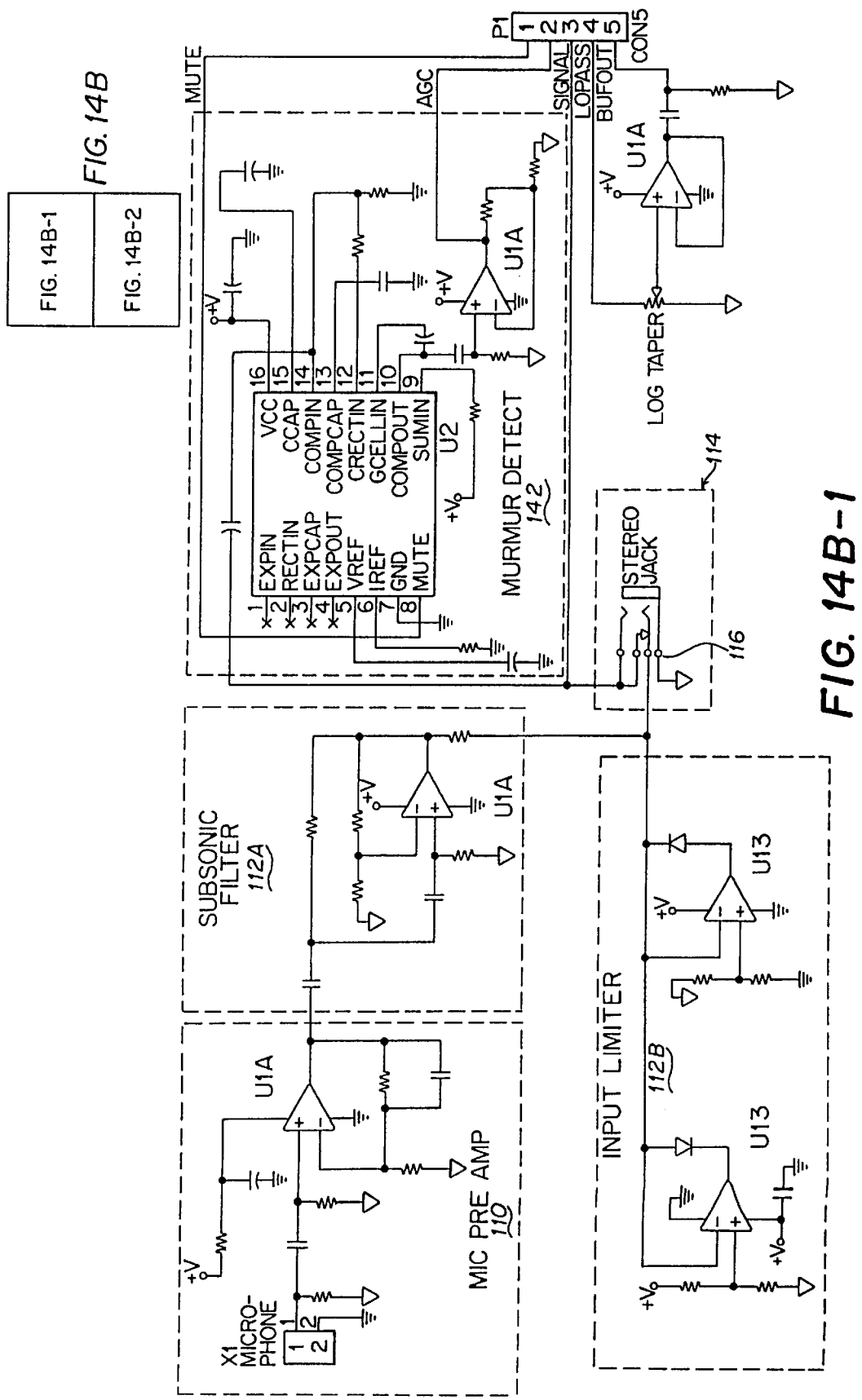
Figures 2, 14B:
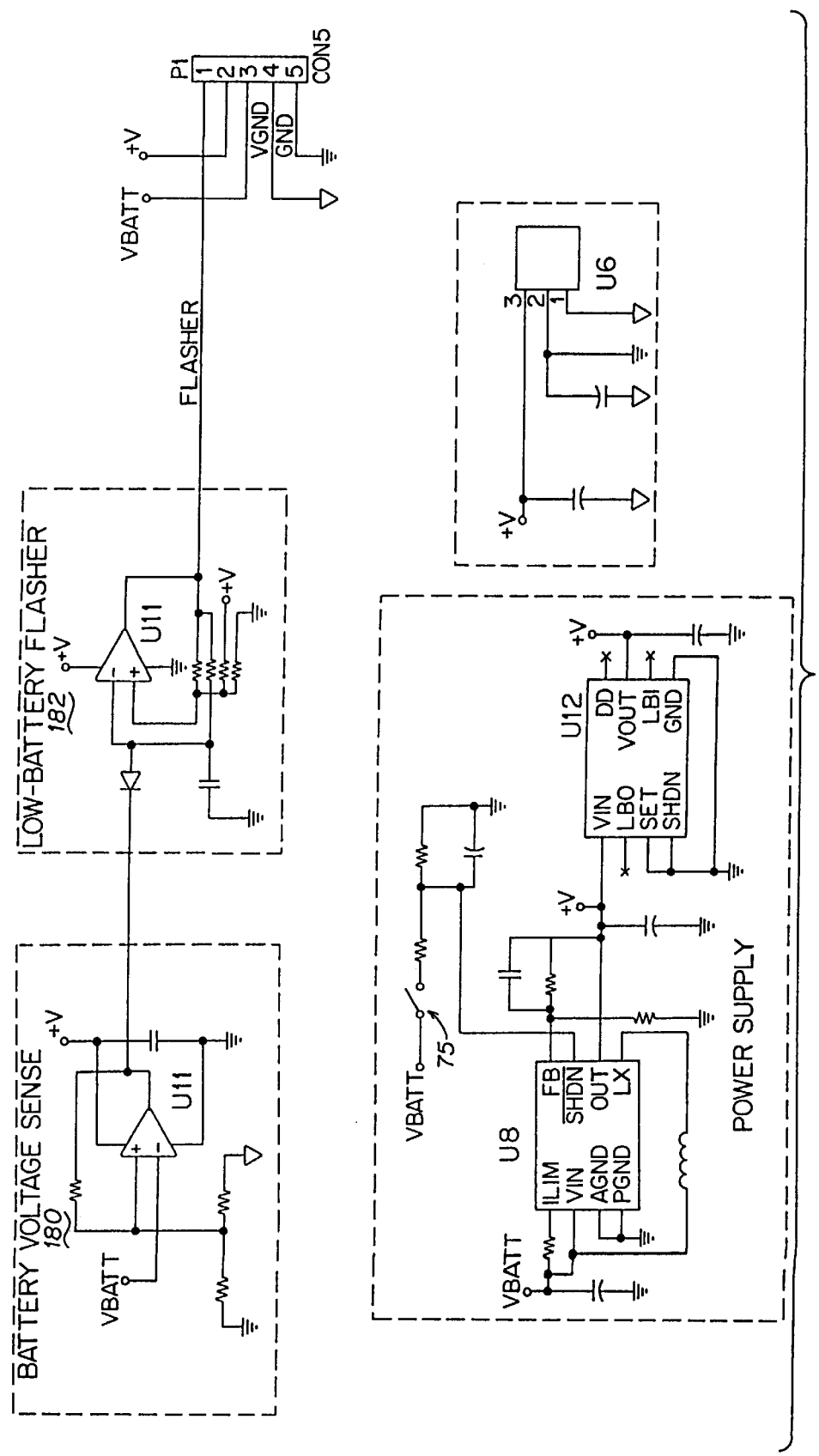

Reference is now made to FIGS. 14A and 14B, which Figures are a schematic diagram of an illustrative circuit embodiment of the block diagram of FIG. 12C. The battery voltage sensing circuit 180 and flasher circuit 182 operate in the same manner as described in connection with FIGS. 13A and 13B. The integrated circuits used in the circuit of FIGS. 14A and 14B are listed below:

| Integrated Circuit List (FIGS 14A and 14B) | | | |
|---|---|---|---|
| IC# | Part # | Manufacturer | Description |
| U1A | MAX494 | Maxim | quad op amp |
| U2 | NE578 | Philips/Signetics | compressor/expander (AGC function) |
| U3 | MAX392 | Maxim | quad switch |
| U4 | LMC555C | National Semiconductor | timer |
| U5 | LTC1164 | Linear Technology | switched capacitor programmable filter |
| U6 | TLE2425C | Texas Instruments | virtual ground generator |
| U7 | 74HC175 | Motorola | quad D flip flop |
| U8 | MAX777 | Maxim | dc to dc converter controller 1 battery cell step-up |
| U9 | LMC660C | National Semiconductor | quad op amp |
| U10 | LMC660C | National Semiconductor | quad op amp |
| U11 | LMC662C | National Semiconductor | dual op amp |
| U12 | MAX667 | Maxim | voltage regulator |
| U13 | MAX492 | Maxim | dual op amp |

One skilled in the art will appreciate that although four operational modes have been described in detail, the electronic stethoscope can be provided with additional operational modes.

In the illustrated embodiments, discrete circuitry has been described in order to select the mode of operation and control of the electronic stethoscope's processing sections. Alternatively, a microcontroller under software control could be used. The use of a microcontroller could allow more than four modes of operation to be selected using the illustrated four mode switches. In addition, the various modes of operation could be combined in ways other than as illustrated. Additionally, a microcontroller could be used to select more specific pass bands for specialty use, for example, by cardiologists or pulmonologists, who might want to listen to specific frequency ranges of the heart and/or lungs. Furthermore, the microcontroller could be used to create modes with user-adjustable corner frequencies using, for example, the volume control 18 to vary the frequency when one of these modes is selected or using the mode buttons as controls for up and down steps of frequency.

A microcontroller could also enable the mode switches to toggle the pediatric mode on and off instead of using a separate switch. In this mode, the microcontroller could also control the lighting of the indicator LED to show the user that pediatric mode had been entered.

A microcontroller could also be used to create a digital volume control which would enable the user to press an up or down button to increase or decrease the output volume. In addition, the microcontroller could enable the user to select a particular reference volume level. The user could then selectively toggle between a volume level set by the variable volume control (either analog or digital) in any mode and the reference volume level (user definable) for comparison of the sounds heard at different volume levels. The microcontroller could also generate a reference heart signal for calibrating and/or setting the reference volume level. This reference level could also be useful in establishing standard grading levels of murmurs between and among doctors with different levels of hearing.

Figure 15:
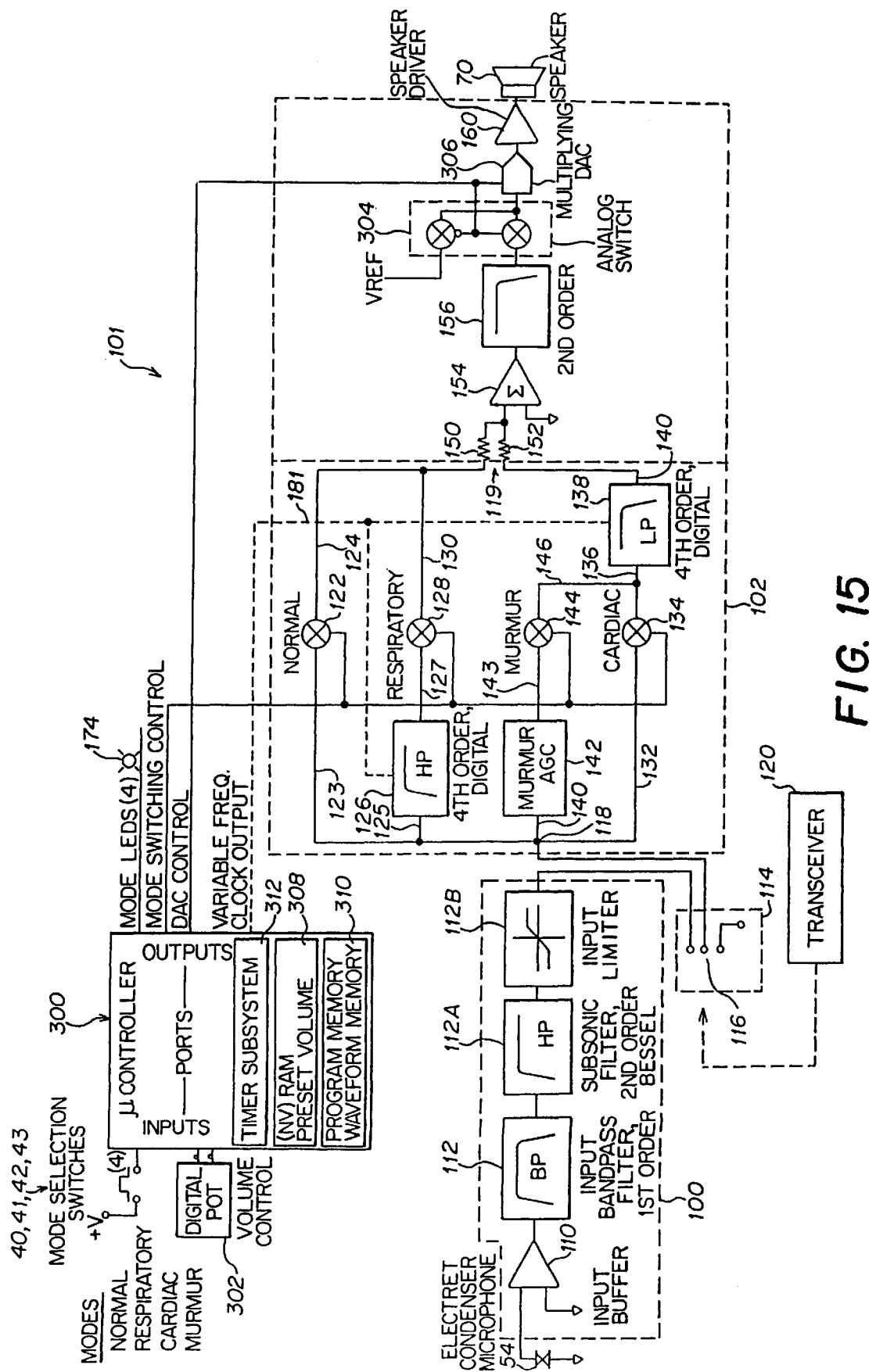
FIG. 15 illustrates another embodiment of the invention.

Reference is now made to FIG. 15, which figure illustrates a circuit implementation of a microcontroller and associated circuitry that provides the aforementioned features and functions. The circuit 101 of FIG. 15 enables the electronic stethoscope to have an internally stored reference heart signal that can be listened to by the user to set a reference volume level that is stored in a nonvolatile memory 308. Once the reference volume level has been selected and stored by the user, the user can toggle between the user-selected variable volume level and the reference volume level (in any mode of operation) to compare sounds heard at an amplified or attenuated level against a reference level. The reference level can be reprogrammed at any time, simply by repeating the calibration procedure described hereinafter. Circuit 101 also allows the volume control 302 (either analog or digital) to also provide a frequency control for continuously varying the corner frequencies of the digital filter in each respective mode of operation.

In one embodiment, microcontroller 300 may be a Microchip 16C73 microcontroller. The microcontroller is used as a central control and timing device and contains an integrated program memory 310, data memory 308, and a clock-timer subsystem 312. The microcontroller 300 provides the interface between the mode switches and the processing section 102. Microcontroller 300 also provides the interface to a pulse generating encoder (for example, control 302) for volume and/or corner frequency adjustment. Microcontroller 300 also acts as the clock generator for the control of the corner frequency adjustment of digital filters 126 and 138. Microcontroller 300 also controls illumination of the mode indication light emitting diodes 174.

Microcontroller 300 also controls a multiplying digital-to-analog converter (DAC) 306 to control the output volume level and for playback of the stored reference heart signal. In one embodiment, the DAC 306 is coupled between an analog switch 304 and output driver 160. DAC 306 may by a Maxim MAX504 which features a serial interface to the microcontroller, low power consumption, and ten-bit resolution. Multiplying DAC 306 scales whatever input level appears at its reference input by a digital word loaded from the microcontroller.

When used as a volume control, DAC 306 is loaded with a static value, and analog switch 304 is used to connect the processed stethoscope signal from low pass filter 156 to the reference input of DAC 306. When playing back the stored reference heart signal waveform, the reference input to DAC 306 is switched to a constant DC voltage, and the microcontroller sequentially loads the DAC with the stored waveform data points from memory 308. The microcontroller then loops through the waveform memory 308, playing back the waveform repeatedly until the mode is changed. The playback volume of the reference heart signal can be varied by scaling the waveform values in the microcontroller prior to loading them into the DAC 306.

To set a reference volume, a calibration procedure is used in which the user selects the reference signal mode, for example, by pressing two of the mode buttons simultaneously. Once this mode has been selected, the electronic stethoscope will repeatedly play back the reference heart signal. The user can then rotate the volume control knob until the desired volume level of the reference signal can be heard in the user's ears. The reference volume level can be stored by pressing one of the mode buttons. The microcontroller 300 then uses the current waveform scaling factor to calculate the static DAC value which is stored in nonvolatile memory 308. This value is used to set the user-selected reference volume when the reference volume mode is selected. The user will then have the ability, when using the stethoscope to listen to a biological signal, to toggle between any volume setting (as determined by manipulation of the volume control) and the stored reference volume level.

In one embodiment, volume control 302 may be a rotary pulse encoder and, as mentioned previously, the rotary pulse encoder can be used to vary the corner frequencies of the digital filter in the respective operational modes. For example, the rotary pulse encoder can be a Bourns ECT1D device. As the rotary pulse encoder's shaft is rotated, two pulse streams that are 90° out of phase with respect to each other are produced. The order of arrival of the pulses at the microcontroller is used to determine if the shaft is being rotated clockwise (for example, increasing volume or frequency) or counter clockwise (for example, decreasing volume or frequency). The shaft is able to rotate continuously, and therefore relative volume or frequency changes are possible from any shaft position. Microcontroller 300 may use DAC 306 to generate an audible tone to indicate if extremes of the variable range are reached. One skilled in the art will appreciate that the microcontroller and associated circuitry may also be used in conjunction with the circuit illustrated in FIG. 12.

Having thus described at least one illustrative embodiment of the invention, various alterations, modifications, and improvements will readily occur to those skilled in the art. Such alterations, modifications, and improvements are intended to be part of this disclosure, and are intended to be within the spirit and scope of the invention. Accordingly, the foregoing description is by way of example only and is not intended as limiting. The invention is limited only as defined in the following claims and the equivalents thereto.

What is claimed is:

1. An electronic stethoscope, comprising:

a chestpiece having a diaphragm for providing acoustic pressure signals;

a first acoustic conduit having a first end acoustically coupled to the diaphragm and a second end acoustically coupled to a first electronic transducer;

a second acoustic conduit having a first end acoustically coupled to the diaphragm and an open second end;

an electronic processing section contained within an enclosure, the enclosure also containing the second end of the first acoustic conduit and the open second end of the second acoustic conduit; and a pair of binaurals acoustically coupled to a second transducer contained within the enclosure.

2. An electronic stethoscope, comprising:

a chestpiece having a diaphragm for providing acoustic pressure signals;

a first acoustic conduit having a first end acoustically coupled to the diaphragm and a first electronic transducer disposed in the first acoustic conduit in proximity to a second end thereof;

a second acoustic conduit having a first end acoustically coupled to the diaphragm and a vent disposed in the second acoustic conduit in proximity to a second end thereof;

a second electronic transducer disposed at the second end of the first acoustic conduit; and a third electronic transducer disposed at the second end of the second acoustic conduit.

3. The electronic stethoscope of claim 2, wherein the stethoscope has a resonant frequency determined by a length of the first acoustic conduit and a length of the second acoustic conduit.

4. An electronic stethoscope, comprising:

a chestpiece having a diaphragm for providing acoustic pressure signals;

a first acoustic conduit having a first end acoustically coupled to the diaphragm and a second end acoustically coupled to a first electronic transducer;

a second acoustic conduit having a first end acoustically coupled to the diaphragm and an open second end;

an electronic processing section contained within an enclosure, the enclosure also containing the second end of the first acoustic conduit; and a pair of binaurals acoustically coupled to a second transducer contained within the enclosure.

5. An electronic stethoscope, comprising:

a chestpiece having a diaphragm for providing acoustic pressure signals;

a first acoustic conduit having a first end acoustically coupled to the diaphragm and a first electronic transducer, the first acoustic conduit having a closed second end;

a second acoustic conduit having a first end acoustically coupled to the diaphragm and the first electronic transducer, the second acoustic conduit having an open second end;

an electronic processing section contained within an enclosure;

a tube, coupling the chestpiece to the enclosure, containing the first acoustic conduit and the second acoustic conduit; and a pair of binaurals acoustically coupled to a second transducer contained within the enclosure.

6. The electronic stethoscope of claim 5, further comprising an acoustically transparent energy dampening foam surrounding the first electronic transducer.

7. The electronic stethoscope of claim 1, 2, 4, or 5, wherein the combined length of the first and second acoustic conduits is approximately determined by the formula:

$$f = \frac{v}{4L}$$

where:

$f$ = the resonant frequency of the stethoscope $v \approx$ the speed of sound (approximately 1132 ft/sec)

$L$ = the length of the first and second acoustic conduits (ft.).

8. The electronic stethoscope of claim 7, wherein the stethoscope has a resonant frequency in the range of 120 Hz to 155 Hz.

9. The electronic stethoscope of claim 8, wherein the resonant frequency of the stethoscope is approximately 121 Hertz.

10. The electronic stethoscope of claim 8, wherein the resonant frequency of the stethoscope is approximately 136 Hertz.

11. The electronic stethoscope of claim 1, 2, 4, or 5, wherein the chestpiece is constructed of aluminum alloy.

12. The electronic stethoscope of claim 11, wherein the diaphragm is constructed of polycarbonate.

13. A stethoscope, comprising:

a chestpiece having a diaphragm for providing acoustic pressure signals;

a first binaural and a second binaural for transmitting acoustic signals;

an acoustic tube coupling the chestpiece to the first binaural and the second binaural;

wherein each of the first binaural and the second binaural has a first curve that substantially follows a shape of a human body from a neck region to a chest region and a second curve that substantially follows a shape of a human body from a base of the neck region to a shoulder region.

14. The stethoscope of claim 13, wherein the first curve has a radius in the range of 3 to 4 inches.

15. The stethoscope of claim 13, wherein the first curve has a radius in the range of 2 to 3 inches.

* * * * *